United States Patent
Cynis et al.

(10) Patent No.: US 8,518,406 B2
(45) Date of Patent: Aug. 27, 2013

(54) ANTIBODIES DIRECTED AGAINST PYROGLUTAMATE MONOCYTE CHEMOATTRACTANT PROTEIN-1 (MCP-1 N1PE)

(75) Inventors: Holger Cynis, Halle/Saale (DE);
Hans-Ulrich Demuth, Halle/Saale (DE);
Jens-Ulrich Rahfeld, Lieskau (DE);
Kathrin Gans, Halle/Saale (DE);
Stephan Schilling, Halle/Saale (DE);
Sonja Kampfer, Germering (DE)

(73) Assignee: Probiodrug AG, Halle-Saale (DE)

( * ) Notice: Subject to any disclaimer, the term of this patent is extended or adjusted under 35 U.S.C. 154(b) by 422 days.

(21) Appl. No.: 12/544,319

(22) Filed: Aug. 20, 2009

(65) Prior Publication Data
US 2010/0119478 A1    May 13, 2010

Related U.S. Application Data

(60) Provisional application No. 61/090,264, filed on Aug. 20, 2008.

(51) Int. Cl.
*A61K 39/395* (2006.01)
*A61K 39/44* (2006.01)
*C07K 16/24* (2006.01)

(52) U.S. Cl.
USPC ............... 424/139.1; 424/141.1; 530/387.9; 530/388.1

(58) Field of Classification Search
None
See application file for complete search history.

(56) References Cited

U.S. PATENT DOCUMENTS
2003/0162737 A1    8/2003 Egashira

FOREIGN PATENT DOCUMENTS

| EP | 1538207 | 6/2005 |
|---|---|---|
| WO | 02/02640 | 1/2002 |
| WO | 2004/016769 | 2/2004 |
| WO | 2006/125201 | 11/2006 |

OTHER PUBLICATIONS

Brown et al. J. Immunol. 156: 3585-3591, 1996.*
Vajdos et al. J. Mol. Biol. 320: 415-428, 2002.*
Beiboer et al. J. Mol. Biol. 296: 833-849, 2000.*
Klimka et al. British J. Can. 83: 252-260, 2000.*
Zhou, Yan et al. Dexamethasone suppresses monocyte chemoattractant protein-1 production via mitogen activated protein kinase phosphatase-1 dependent inhibition of Jun N-terminal kinase and p38 mitogen-activated protein kinase in activated rat microglia, Journal of Neurochemistry, 2007 vol. 102 pp. 667-678.
Gong, Jiang-Hong et al. Antagonists of Monocyte Chermattractant Protein 1 Identified by Modification of Functionally Critical NH2-terminal Residues J. Experim Med. 1995 vol. 181, pp. 631-640.
Jarnagin, Kurt et al. Identification of Surface Residues of the Monocyte Chemotactic Protein 1 that Affect Signaling through the Receptor CCR2, Biochemistry 1999 vol. 38 pp. 16167-16177.
Kesavan, Prabakaran et al. Anti-Angiogenic and Anti-Cancer Activity of Monoclonal Antibodies to CCL-2/MCP-1 (Monocyte Chemoattractant Protein-1) J Immunotherapy. vol. 27, No. 6, Nov./Dec. 2004 pp. S11-S12.
Kruszynski, Marian et al., Synthesis and biological characterization of human monocyte chemoattractant protein 1 (MCP-1) and its analogs. Journal of Peptide Science 2006 vol. 12 pp. 25-32.
Yoshimura, Teizo et al. Production and Characterization of Mouse Monoclonal Antibodies Against Human Monocyte Chemoattractant Protein-1, The Journal of Immunology 1991 vol. 147 pp. 2229-2233.

* cited by examiner

*Primary Examiner* — Christine J Saoud
(74) *Attorney, Agent, or Firm* — Dentons US LLP

(57) ABSTRACT

Monoclonal antibodies which bind specifically to the proinflammatory cytokine pyroglutamate MCP-1 (MCP-1 N1pE) are described.

26 Claims, 23 Drawing Sheets

FIGURES

SEQUENCE LISTING

```
<160> NUMBER OF SEQ ID NOS: 44

<210> SEQ ID NO 1
<211> LENGTH: 99
<212> TYPE: PRT
<213> ORGANISM: Homo sapiens

<400> SEQUENCE: 1

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 2
<211> LENGTH: 300
<212> TYPE: DNA
<213> ORGANISM: Homo sapiens

<400> SEQUENCE: 2
atgaaagtct ctgccgccct tctgtgcctg ctgctcatag cagccacctt cattccccaa      60
gggctcgctc agccagatgc aatcaatgcc ccagtcacct gctgttataa cttcaccaat     120
aggaagatct cagtgcagag gctcgcgagc tatagaagaa tcaccagcag caagtgtccc     180
aaagaagctg tgatcttcaa gaccattgtg gccaaggaga tctgtgctga ccccaagcag     240
aagtgggttc aggattccat ggaccacctg gacaagcaaa cccaaactcc gaagacttga     300

<210> SEQ ID NO 3
<211> LENGTH: 4
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: pyroglutamate

<400> SEQUENCE: 3

Glu Pro Asp Ala
1

<210> SEQ ID NO 4
```

-continued

```
<211> LENGTH: 38
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: pyroglutamate

<400> SEQUENCE: 4

Glu Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys
        35

<210> SEQ ID NO 5
<211> LENGTH: 36
<212> TYPE: PRT
<213> ORGANISM: Homo sapiens

<400> SEQUENCE: 5

Asp Ala Ile Asn Ala Pro Val Thr Cys Cys Tyr Asn Phe Thr Asn Arg
1               5                   10                  15

Lys Ile Ser Val Gln Arg Leu Ala Ser Tyr Arg Arg Ile Thr Ser Ser
            20                  25                  30

Lys Cys Pro Lys
        35

<210> SEQ ID NO 6
<211> LENGTH: 10
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: pyroglutamate

<400> SEQUENCE: 6

Glu Pro Asp Ala Ile Asn Ala Pro Val Cys
1               5                   10

<210> SEQ ID NO 7
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 7
atgaagttgc ctgttaggct gttggtgctg                                    30

<210> SEQ ID NO 8
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 8
atggagwcag acacactcct gytatgggtg                                    30

<210> SEQ ID NO 9
<211> LENGTH: 30
<212> TYPE: DNA
<213> ORGANISM: Artificial sequence
```

```
<220> FEATURE:
<223> OTHER INFORMATION: Synthetic Oligonucleotide

<400> SEQUENCE: 9
atgagtgtgc tcactcaggt cctggsgttg                                          30

<210> SEQ ID NO 10
<211> LENGTH: 33
<212> TYPE: DNA
<213> ORGANISM: Artificial sequence
<220> FEATURE:
<223> OTHER INFORMATION: Synthetic Oligonucleotide

<400> SEQUENCE: 10
atgaggrccc ctgctcagwt tyttggmwtc ttg                                      33

<210> SEQ ID NO 11
<211> LENGTH: 30
<212> TYPE: DNA
<213> ORGANISM: Artificial sequence
<220> FEATURE:
<223> OTHER INFORMATION: Synthetic Oligonucleotide

<400> SEQUENCE: 11
atggatttwc aggtgcagat twtcagcttc                                          30

<210> SEQ ID NO 12
<211> LENGTH: 27
<212> TYPE: DNA
<213> ORGANISM: Artificial sequence
<220> FEATURE:
<223> OTHER INFORMATION: Synthetic Oligonucleotide

<400> SEQUENCE: 12
atgaggtkcy ytgytsagyt yctgrgg                                             27

<210> SEQ ID NO 13
<211> LENGTH: 31
<212> TYPE: DNA
<213> ORGANISM: Artificial sequence
<220> FEATURE:
<223> OTHER INFORMATION: Synthetic Oligonucleotide

<400> SEQUENCE: 13
atgggcwtca agatggagtc acakwyycwg g                                        31

<210> SEQ ID NO 14
<211> LENGTH: 31
<212> TYPE: DNA
<213> ORGANISM: Artificial sequence
<220> FEATURE:
<223> OTHER INFORMATION: Synthetic Oligonucleotide

<400> SEQUENCE: 14 atgtgggay ctktttycmm tttttcaatt g                                         31

<210> SEQ ID NO 15
<211> LENGTH: 25
<212> TYPE: DNA
<213> ORGANISM: Artificial sequence
<220> FEATURE:
<223> OTHER INFORMATION: Synthetic Oligonucleotide

<400> SEQUENCE: 15
atggtrtccw casctcagtt ccttg                                               25
```

```
<210> SEQ ID NO 16
<211> LENGTH: 27
<212> TYPE: DNA
<213> ORGANISM: Artificial sequence
<220> FEATURE:
<223> OTHER INFORMATION: Synthetic Oligonucleotide

<400> SEQUENCE: 16
atgtatatat gtttgttgtc tatttct                                           27

<210> SEQ ID NO 17
<211> LENGTH: 28
<212> TYPE: DNA
<213> ORGANISM: Artificial sequence
<220> FEATURE:
<223> OTHER INFORMATION: Synthetic Oligonucleotide

<400> SEQUENCE: 17
atggaagccc cagctcagct tctcttcc                                          28

<210> SEQ ID NO 18
<211> LENGTH: 20
<212> TYPE: DNA
<213> ORGANISM: Artificial sequence
<220> FEATURE:
<223> OTHER INFORMATION: Synthetic Oligonucleotide

<400> SEQUENCE: 18
actggatggt gggaagatgg                                                   20

<210> SEQ ID NO 19
<211> LENGTH: 27
<212> TYPE: DNA
<213> ORGANISM: Artificial sequence
<220> FEATURE:
<223> OTHER INFORMATION: Synthetic Oligonucleotide

<400> SEQUENCE: 19
atgaaatgca gctggggcat sttcttc                                           27

<210> SEQ ID NO 20
<211> LENGTH: 26
<212> TYPE: DNA
<213> ORGANISM: Artificial sequence
<220> FEATURE:
<223> OTHER INFORMATION: Synthetic Oligonucleotide

<400> SEQUENCE: 20
atgggatgga gctrtatcat sytctt                                            26

<210> SEQ ID NO 21
<211> LENGTH: 27
<212> TYPE: DNA
<213> ORGANISM: Artificial sequence
<220> FEATURE:
<223> OTHER INFORMATION: Synthetic Oligonucleotide

<400> SEQUENCE: 21
atgaagwtgt ggttaaactg ggttttt                                           27

<210> SEQ ID NO 22
<211> LENGTH: 25
<212> TYPE: DNA
<213> ORGANISM: Artificial sequence
<220> FEATURE:
<223> OTHER INFORMATION: Synthetic Oligonucleotide

<400> SEQUENCE: 22
```

-continued atgractttg ggytcagctt grttt    25

<210> SEQ ID NO 23
<211> LENGTH: 30
<212> TYPE: DNA
<213> ORGANISM: Artificial sequence
<220> FEATURE:
<223> OTHER INFORMATION: Synthetic Oligonucleotide

<400> SEQUENCE: 23
atggactcca ggctcaattt agttttcctt    30

<210> SEQ ID NO 24
<211> LENGTH: 28
<212> TYPE: DNA
<213> ORGANISM: Artificial sequence
<220> FEATURE:
<223> OTHER INFORMATION: Synthetic Oligonucleotide

<400> SEQUENCE: 24
atggcttgtc ytrgsgctrc tcttctgc    28

<210> SEQ ID NO 25
<211> LENGTH: 26
<212> TYPE: DNA
<213> ORGANISM: Artificial sequence
<220> FEATURE:
<223> OTHER INFORMATION: Synthetic Oligonucleotide

<400> SEQUENCE: 25
atggratgga gckggrtctt tmtctt    26

<210> SEQ ID NO 26
<211> LENGTH: 23
<212> TYPE: DNA
<213> ORGANISM: Artificial sequence
<220> FEATURE:
<223> OTHER INFORMATION: Synthetic Oligonucleotide

<400> SEQUENCE: 26
atgagagtgc tgattctttt gtg    23

<210> SEQ ID NO 27
<211> LENGTH: 30
<212> TYPE: DNA
<213> ORGANISM: Artificial sequence
<220> FEATURE:
<223> OTHER INFORMATION: Synthetic Oligonucleotide

<400> SEQUENCE: 27
atggmttggg tgtggamctt gctattcctg    30

<210> SEQ ID NO 28
<211> LENGTH: 27
<212> TYPE: DNA
<213> ORGANISM: Artificial sequence
<220> FEATURE:
<223> OTHER INFORMATION: Synthetic Oligonucleotide

<400> SEQUENCE: 28
atgggcagac ttacattctc attcctg    27

<210> SEQ ID NO 29
<211> LENGTH: 28
<212> TYPE: DNA
<213> ORGANISM: Artificial sequence

```
<220> FEATURE:
<223> OTHER INFORMATION: Synthetic Oligonucleotide

<400> SEQUENCE: 29
atggattttg ggctgatttt ttttattg                                          28

<210> SEQ ID NO 30
<211> LENGTH: 27
<212> TYPE: DNA
<213> ORGANISM: Artificial sequence
<220> FEATURE:
<223> OTHER INFORMATION: Synthetic Oligonucleotide

<400> SEQUENCE: 30
atgatggtgt taagtcttct gtacctg                                           27

<210> SEQ ID NO 31
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 31
cagtggatag acagatgggg g                                                 21

<210> SEQ ID NO 32
<211> LENGTH: 21
<212> TYPE: DNA
<213> ORGANISM: Artificial sequence
<220> FEATURE:
<223> OTHER INFORMATION: Synthetic Oligonucleotide

<400> SEQUENCE: 32
cagtggatag actgatgggg g                                                 21

<210> SEQ ID NO 33
<211> LENGTH: 435
<212> TYPE: DNA
<213> ORGANISM: Mus musculus

<400> SEQUENCE: 33
atggagtcac agtttctgtt tctgttagtg ctctggattc gggaaaccaa cggtgatgtt        60
gtgatgaccc agactcccct cagtttgtcg gttaccattg acaaccagc ctccatctct        120 tgcaagtcaa gtcagagcct cttagatagt gctggaaaga catatttgag ttggttgtta       180
cagaggccag gccagtctcc aaagcgccta atctatctgg tgtctaaact ggactctgga       240
gtccctgaca ggttcactgg cagtggatca gggacagatt tcacactgaa aatcagcaga       300
gtggaggctg aggatttggg agtttattac tgctggcaag gtacacattt tccgtggacg       360
ttcggtggag gcaccaagct ggaaatcaaa cgggctgatg ctgcaccaac tgtatccatc       420
ttcccaccat ccagt                                                       435

<210> SEQ ID NO 34
<211> LENGTH: 145
<212> TYPE: PRT
<213> ORGANISM: Mus musculus

<400> SEQUENCE: 34

Met Glu Ser Gln Phe Leu Phe Leu Leu Val Leu Trp Ile Arg Glu Thr
1               5                   10                  15

Asn Gly Asp Val Val Met Thr Gln Thr Pro Leu Ser Leu Ser Val Thr
            20                  25                  30
```

Ile Gly Gln Pro Ala Ser Ile Ser Cys Lys Ser Ser Gln Ser Leu Leu
            35                  40                  45

Asp Ser Ala Gly Lys Thr Tyr Leu Ser Trp Leu Leu Gln Arg Pro Gly
 50                  55                  60

Gln Ser Pro Lys Arg Leu Ile Tyr Leu Val Ser Lys Leu Asp Ser Gly
 65                  70                  75                  80

Val Pro Asp Arg Phe Thr Gly Ser Gly Ser Gly Thr Asp Phe Thr Leu
                 85                  90                  95

Lys Ile Ser Arg Val Glu Ala Glu Asp Leu Gly Val Tyr Tyr Cys Trp
            100                 105                 110

Gln Gly Thr His Phe Pro Trp Thr Phe Gly Gly Gly Thr Lys Leu Glu
            115                 120                 125

Ile Lys Arg Ala Asp Ala Ala Pro Thr Val Ser Ile Phe Pro Pro Ser
    130                 135                 140

Ser
145

<210> SEQ ID NO 35
<211> LENGTH: 427
<212> TYPE: DNA
<213> ORGANISM: Mus musculus

<400> SEQUENCE: 35
atggaatgga gcggggtctt tctcttcctc ttgtcaggaa ctgcaggtgt ccactctgag      60
gtccagctgc aacagtctgg acctgagctg gtgaagcctg ggcttcagt gaagatgtcc     120 tgtaaggctt ctggatacac attcactgac tactacatgg actgggtgaa gcagagccat     180
ggagaaagct ttgagtgcat tggacgtgtt aatccttaca atggtggtac tagctacaac     240
cagaagttca aggcaaggc cacattgact gttgacaagt cctccagcac agcctacatg     300
gagctcaaca gcctgacatc tgaggactct gcggtctatt actgtgcaag gctcggtagt     360
agctaccgct ggggccaagg caccactctc acagtctcct cagccaaaac aacacccca     420 tcagtct                                                              427

<210> SEQ ID NO 36
<211> LENGTH: 142
<212> TYPE: PRT
<213> ORGANISM: Mus musculus

<400> SEQUENCE: 36

Met Glu Trp Ser Gly Val Phe Leu Phe Leu Leu Ser Gly Thr Ala Gly
 1               5                  10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Asp Tyr Tyr Met Asp Trp Val Lys Gln Ser His Gly Glu Ser Phe
 50                  55                  60

Glu Cys Ile Gly Arg Val Asn Pro Tyr Asn Gly Gly Thr Ser Tyr Asn
 65                  70                  75                  80

Gln Lys Phe Lys Gly Lys Ala Thr Leu Thr Val Asp Lys Ser Ser Ser
                 85                  90                  95

Thr Ala Tyr Met Glu Leu Asn Ser Leu Thr Ser Glu Asp Ser Ala Val
            100                 105                 110

Tyr Tyr Cys Ala Arg Leu Gly Ser Ser Tyr Arg Trp Gly Gln Gly Thr
            115                 120                 125

Thr Leu Thr Val Ser Ser Ala Lys Thr Thr Pro Pro Ser Val
    130                 135                 140

<210> SEQ ID NO 37
<211> LENGTH: 441
<212> TYPE: DNA
<213> ORGANISM: Mus musculus

<400> SEQUENCE: 37
atggtgtcct cagctcagtt cctgtttctg ttagtgctct ggattcggga aaccaacggt      60
gatgttgtga tgacccagac tccectcagt ttgtcggtta ccattggaca accagcctcc    120
atctcttgca agtcaagtca gagcctctta gatagtgctg gaaagacata tttgagttgg    180
ttgttacaga ggccaggcca gtctccaaag cgcctaatct atctggtgtc taaactggac    240
tctggagtcc ctgacaggtt cactggcagt ggatcaggga cagatttcac actgaaaatc    300
agcagagtgg aggctgagga tttgggagtt tattactgct ggcaaggtac acattttccg    360
tggacgttcg gtggaggcac aagctggaa atcaaacggg ctgatgctgc accaactgta    420
tccatcttcc caccatccag t                                              441

<210> SEQ ID NO 38
<211> LENGTH: 147
<212> TYPE: PRT
<213> ORGANISM: Mus musculus

<400> SEQUENCE: 38

Met Val Ser Ser Ala Gln Phe Leu Phe Leu Leu Val Leu Trp Ile Arg
1               5                   10                  15

Glu Thr Asn Gly Asp Val Val Met Thr Gln Thr Pro Leu Ser Leu Ser
            20                  25                  30

Val Thr Ile Gly Gln Pro Ala Ser Ile Ser Cys Lys Ser Ser Gln Ser
        35                  40                  45

Leu Leu Asp Ser Ala Gly Lys Thr Tyr Leu Ser Trp Leu Leu Gln Arg
    50                  55                  60

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Trp Gln Gly Thr His Phe Pro Trp Thr Phe Gly Gly Gly Thr Lys
        115                 120                 125

Leu Glu Ile Lys Arg Ala Asp Ala Ala Pro Thr Val Ser Ile Phe Pro
    130                 135                 140

Pro Ser Ser
145

<210> SEQ ID NO 39
<211> LENGTH: 435
<212> TYPE: DNA
<213> ORGANISM: Mus musculus

<400> SEQUENCE: 39
atggaatgga gcgggatctt tatcttcctc ttgtcaggaa ctgcaggtgt ccactctgag      60
gtccagctgc aacagtctgg acctgagctg gtgaagcctg gggcttcagt gaagatgtcc    120
tgtaaggctt ctggatacac attcactgac tactacatgg actgggtgaa gcagagccat    180

```
ggagaaagct  ttgagtgcat  tggacgtgtt  aatccttaca  atggtggtac  tagctacaac      240
cagaagttca  agggcaaggc  cacattgact  gttgacaagt  cctccagcac  agcctacatg      300
gagctcaaca  gcctgacatc  tgaggactct  gcggtctatt  actgtgcaag  gctcggtagt      360
agctaccgct  ggggccaagg  caccactctc  acagtctcct  cagccaaaac  aacacccccca    420 tcagtctatc  cactg                                                          435

<210> SEQ ID NO 40
<211> LENGTH: 145
<212> TYPE: PRT
<213> ORGANISM: Mus musculus

<400> SEQUENCE: 40

Met Glu Trp Ser Gly Ile Phe Ile Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Asp Tyr Tyr Met Asp Trp Val Lys Gln Ser His Gly Glu Ser Phe
    50                  55                  60

Glu Cys Ile Gly Arg Val Asn Pro Tyr Asn Gly Gly Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Asn Ser Leu Thr Ser Glu Asp Ser Ala Val
            100                 105                 110

Tyr Tyr Cys Ala Arg Leu Gly Ser Ser Tyr Arg Trp Gly Gln Gly Thr
        115                 120                 125

Thr Leu Thr Val Ser Ser Ala Lys Thr Thr Pro Pro Ser Val Tyr Pro
    130                 135                 140

Leu
145

<210> SEQ ID NO 41
<211> LENGTH: 438
<212> TYPE: DNA
<213> ORGANISM: Mus musculus

<400> SEQUENCE: 41
atgaagttgc  ctgttaggct  gttggtgctg  atgttctgga  ttcctgcttc  cagcagtgat       60
gttttgatga  cccaaactcc  actctccctg  cctgtcagtc  ttggagatca  agcctccatc      120
tcttgcaaat  ctagtcagag  cattgtacat  agtaatggaa  acacctattt  agaatggtac      180
ctgcagaaac  caggccagtc  tccaaagctc  ctgatctaca  aagttttcaa  ccgattttct      240
ggggtcccag  acaggttcag  tggcagtgga  tcagggacag  atttcacact  caagatcagc      300
agagtggagg  ctgaggatct  gggagtttat  tactgctttc  aaggttcaca  tgttccgtac      360
acgttcggag  gggggaccaa  gctggaaata  aaacgggctg  atgctgcacc  aactgtatcc      420
atcttcccac  catccagt                                                        438

<210> SEQ ID NO 42
<211> LENGTH: 146
<212> TYPE: PRT
<213> ORGANISM: Mus musculus

<400> SEQUENCE: 42
```

```
Met Lys Leu Pro Val Arg Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Lys Ser Ser Gln Ser Ile
        35                  40                  45

Val His Ser Asn Gly Asn Thr Tyr Leu Glu Trp Tyr Leu Gln Lys Pro
50                  55                  60

Gly Gln Ser Pro Lys Leu Leu Ile Tyr Lys Val Phe Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Tyr Thr Phe Gly Gly Gly Thr Lys Leu
        115                 120                 125

Glu Ile Lys Arg Ala Asp Ala Ala Pro Thr Val Ser Ile Phe Pro Pro
130                 135                 140

Ser Ser
145

<210> SEQ ID NO 43
<211> LENGTH: 450
<212> TYPE: DNA
<213> ORGANISM: Mus musculus

<400> SEQUENCE: 43
atgggatgga gcggggtctt tattttaatc ctgtcagtaa ctacaggtgt ccactctgag      60
gtccagctgc agcagtctgg acctgagctg gagaagcctg gcgcttcagt gaagatatcc    120
tgcaaggctt ctggttactc attcactggc tacaacatga actgggtgaa gcagaacaat    180
ggaaagagcc ttgagtggat tggaaatatt actccttact atggtagtac tagctacaac    240
cagaagttca aggcagggt cacattgact gtggacaaat cctccagcac agcctacatg    300
cagctcaaga gcctgacatc tgaggactct gcagtctatt tctgcctcct atggttacga    360
cggggggact atgctatgga ctactgggt caaggaacct cagtcaccgt ctcctcagcc    420
aaaacgacac cccatctgt ctatccactg                                      450

<210> SEQ ID NO 44
<211> LENGTH: 150
<212> TYPE: PRT
<213> ORGANISM: Mus musculus

<400> SEQUENCE: 44

Met Gly Trp Ser Gly Val Phe Ile Leu Ile Leu Ser Val Thr Thr Gly
1               5                   10                  15

Val His Ser Glu Val Gln Leu Gln Gln Ser Gly Pro Glu Leu Glu Lys
            20                  25                  30

Pro Gly Ala Ser Val Lys Ile Ser Cys Lys Ala Ser Gly Tyr Ser Phe
        35                  40                  45

Thr Gly Tyr Asn Met Asn Trp Val Lys Gln Asn Asn Gly Lys Ser Leu
50                  55                  60

Glu Trp Ile Gly Asn Ile Thr Pro Tyr Tyr Gly Ser Thr Ser Tyr Asn
65                  70                  75                  80

Gln Lys Phe Lys Gly Arg Val Thr Leu Thr Val Asp Lys Ser Ser Ser
            85                  90                  95
```

-continued

```
Thr Ala Tyr Met Gln Leu Lys Ser Leu Thr Ser Glu Asp Ser Ala Val
            100                 105                 110

Tyr Phe Cys Leu Leu Trp Leu Arg Arg Gly Asp Tyr Ala Met Asp Tyr
            115                 120                 125

Trp Gly Gln Gly Thr Ser Val Thr Val Ser Ser Ala Lys Thr Thr Pro
            130                 135                 140

Pro Ser Val Tyr Pro Leu
145                 150
```

ANTIBODIES DIRECTED AGAINST PYROGLUTAMATE MONOCYTE CHEMOATTRACTANT PROTEIN-1 (MCP-1 N1PE)

CROSS-REFERENCE TO RELATED APPLICATIONS

This application claims priority from U.S. Provisional Application Ser. No. 61/090,264 filed on Aug. 20, 2008, which is incorporated herein by reference in its entirety to the extent permitted by law.

INCORPORATION-BY-REFERENCE OF SEQUENCE LISTING

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present invention relates to monoclonal antibodies which bind specifically to the proinflammatory cytokine pyroglutamate MCP-1 (MCP-1 N1pE).

BACKGROUND OF THE INVENTION

Chemotactic cytokines (chemokines) are proteins that attract and activate leukocytes and are thought to play a fundamental role in inflammation. Chemokines are divided into four groups categorized by the appearance of N-terminal cysteine residues ("C"-; "CC"-; "CXC"- and "CX3C"- chemokines). "CXC"-chemokines preferentially act on neutrophils. In contrast, "CC"-chemokines attract preferentially monocytes to sites of inflammation. Monocyte infiltration is considered to be a key event in a number of disease conditions (Gerard, C. and Rollins, B. J. (2001) *Nat. Immunol* 2, 108-115; Bhatia, M., et al., (2005) Pancreatology. 5, 132-144; Kitamoto, S., Egashira, K., and Takeshita, A. (2003) *J Pharmacol Sci.* 91, 192-196).

The MCP family, as one family of chemokines, consists of four members (MCP-1 to 4), displaying a preference for attracting monocytes but showing differences in their potential (Luini, W., et al., (1994) *Cytokine* 6, 28-31; Uguccioni, M., et al., (1995) *Eur J Immunol* 25, 64-68).

MCP-1 is a member of the β (C-C) subfamily of chemokines. In this family, the 2 cysteines nearest to the amino terminus are adjacent to each other (thus C-C proteins). As with many other C-C chemokines, the MCP-1 gene is located on chromosome 17 in humans. The cell surface receptors that bind MCP-1 are CCR2 and CCR5.

In the following both cDNA as well as amino acid sequences of MCP-1 are indicated:
Human MCP-1 (CCL2) (GeneBank Accession: M24545)

Protein (Signal Sequence in bold: 23 aa; Mature MCP-1: 76 aa)

SEQ ID NO: 1
KVSAALLCLLLIAATFIPQGLAQPDAINAPVTCCYNFTNRKISVQRLASY

RRITSSKCPKEAVIFKTIVAKEICADPKQKWVQDSMDHLDKQTQTPKT

Consistent with it being a member of the chemokine β family, MCP-1 has been shown to chemoattract and activate monocytes in vitro at subnanomolar concentrations. Elevated MCP-1 expression has been detected in a variety of pathologic conditions that involve monocyte accumulation and activation, including a number of inflammatory and non-inflammatory disease states, like rheumatoid arthritis, atherosclerosis, asthma and delayed hypersensitivity reactions.

A number of studies have underlined in particular the crucial role of MCP-1 for the development of atherosclerosis (Gu, L., et al., (1998) Mol. Cell 2, 275-281; Gosling, J., et al., (1999) J Clin. Invest 103, 773-778); rheumatoid arthritis (Gong, J. H., et al., (1997) J Exp. Med 186, 131-137; Ogata, H., et al., (1997) J Pathol. 182, 106-114); pancreatitis (Bhatia, M., et al., (2005) Am. J Physiol Gastrointest. Liver Physiol 288, G1259-G1265); Alzheimer's disease (Yamamoto, M., et al., (2005) Am. J Pathol. 166, 1475-1485); lung fibrosis (Inoshima, I., et al., (2004) Am. J Physiol Lung Cell Mol. Physiol 286, L1038-L1044); renal fibrosis (Wada, T., et al., (2004) J Am. Soc. Nephrol. 15, 940-948), and graft rejection (Saiura, A., et al., (2004) Arterioscler. Thromb. Vasc. Biol. 24, 1886-1890). Furthermore, MCP-1 might also play a role in gestosis (Katabuchi, H., et al., (2003) Med Electron Microsc. 36, 253-262), as a paracrine factor in tumor development (Ohta, M., et al., (2003) Int. J Oncol. 22, 773-778; Li, S., et al., (2005) J Exp. Med 202, 617-624), neuropathic pain (White, F. A., et al., (2005) Proc. Natl. Acad. Sci. U.S.A) and AIDS (Park, I. W., Wang, J. F., and Groopman, J. E. (2001) Blood 97, 352-358; Coll, B., et al., (2006) Cytokine 34, 51-55).

The mature form of human and rodent MCP-1 is post-translationally modified by Glutaminyl Cyclase (QC) to possess an N-terminal pyroglutamyl (pGlu) residue.

Glutaminyl cyclase (QC, EC 2.3.2.5) catalyzes the intramolecular cyclization of N-terminal glutaminyl residues into pyroglutamic acid (5-oxo-proline, pGlu*) under liberation of ammonia and the intramolecular cyclization of N-terminal glutamyl residues into pyroglutamic acid under liberation of water.

The N-terminal pGlu modification makes the protein resistant against N-terminal degradation by aminopeptidases, which is of importance, since chemotactic potency of MCP-1 is mediated by its N-terminus (Van Damme, J., et al., (1999) Chem Immunol 72, 42-56). Artificial elongation or degradation leads to a loss of function although MCP-1 still binds to its receptor (CCR2) (Proost, P., et al., (1998), J Immunol 160, 4034-4041; Zhang, Y. J., et al., 1994, J Biol. Chem 269, cDNA (300 bp)

SEQ ID NO: 2
```
  1 atgaaagtct ctgccgccct tctgtgcctg ctgctcatag cagccacctt cattccccaa 61 gggctcgctc agccagatgc aatcaatgcc ccagtcacct gctgttataa cttcaccaat 121 aggaagatct cagtgcagag gctcgcgagc tatagaagaa tcaccagcag caagtgtccc 181 aaagaagctg tgatcttcaa gaccattgtg gccaaggaga tctgtgctga ccccaagcag 241 aagtgggttc aggattccat ggaccacctg gacaagcaaa cccaaactcc gaagacttga
```

15918-15924; Masure, S., et al., 1995, J Interferon Cytokine Res. 15, 955-963; Hemmerich, S., et al., (1999) Biochemistry 38, 13013-13025).

Due to the major role of MCP-1 in a number of disease conditions, a potent diagnostic tool and an anti-MCP-1 strategy is required.

As mentioned above, compelling evidence points to a role of MCP 1 in Alzheimer's disease (AD) (Xia, M. Q. and Hyman, B. T. (1999) J Neurovirol. 5, 32-41). The presence of MCP-1 in senile plaques and in reactive microglia, the residential macrophages of the CNS, has been observed in brains of patients suffering from AD (Ishizuka, K., et al., (1997) Psychiatry Clin. Neurosci. 51, 135-138. Stimulation of monocytes and microglia with Amyloid-β protein (Aβ) induces chemokine secretion in vitro (Meda, L., et al., (1996) J Immunol 157, 1213-1218; Szczepanik, A. M., et al., (2001) J Neuroimmunol. 113, 49-62) and intracerebroventricular infusion of Aβ (1-42) into murine hippocampus significantly increases MCP-1 in vivo. Moreover, Aβ deposits attract and activate microglial cells and force them to produce inflammatory mediators such as MCP-1, which in turn leads to a feed back to induce further chemotaxis, activation and tissue damage. At the site of Aβ deposition, activated microglia also phagocytose Aβ peptides leading to an amplified activation (Rogers, J. and Lue, L. F. (2001) Neurochem. Int. 39, 333-340).

Examination of chemokine expression in the 3xTg mouse model for AD revealed that neuronal inflammation precedes plaque formation and MCP-1 is upregulated by a factor of 11. Furthermore, the upregulation of MCP-1 seems to correlate with the occurrence of first intracellular Aβ deposits (Janelsins, M. C., et al., (2005) J Neuroinflammation. 2, 23). Crossbreeding of the Tg2575 mouse model for AD with a MCP-1 overexpressing mouse model has shown an increased microglia accumulation around Aβ deposits and that this accumulation was accompanied by increased amount of diffuse plaques compared to single-transgenic Tg2576 littermates (Yamamoto, M., et al. (2005) Am. J Pathol. 166, 1475-1485).

MCP-1 levels are increased in CSF of AD patients and patients showing mild cognitive impairment (MCI) (Galimberti, D., et al., (2006) Arch. Neurol. 63, 538-543). Furthermore, MCP-1 shows an increased level in serum of patients with MCI and early AD (Clerici, F., et al., (2006) Neurobiol. Aging 27, 1763-1768).

Atherosclerotic lesions, which limit or obstruct coronary blood flow, are the major cause of ischemic heart disease related mortality, resulting in 500,000-600,000 deaths annually. Percutaneous transluminal coronary angioplasty (PTCA) to open the obstructed artery was performed in over 550,000 patients in the U.S. and 945, 000+ patients worldwide in 1996 (Lemaitre et al., 1996). A major limitation of this technique is the problem of post-PTCA closure of the vessel, both immediately after PTCA (acute occlusion) and in the long term (restenosis): 30% of patients with subtotal lesions and 50% of patients with chronic total lesions will go on to restenosis after angioplasty. Additionally, restenosis is a significant problem in patients undergoing saphenous vein bypass graft. The mechanism of acute occlusion appears to involve several factors and may result from vascular recoil with resultant closure of the artery and/or deposition of blood platelets along the damaged length of the newly opened blood vessel followed by formation of a fibrin/red blood cell thrombus.

Restenosis after angioplasty is a more gradual process and involves initial formation of a subcritical thrombosis with release from adherent platelets of cell derived growth factors with subsequent proliferation of intimal smooth muscle cells and local infiltration of inflammatory cells contributing to vascular hyperplasia. It is important to note that multiple processes, among those thrombosis, cell proliferation, cell migration and inflammation each seem to contribute to the restenotic process.

In the U.S., a 30-50% restenosis rate translates to 120,000-200,000 U.S. patients at risk from restenosis. If only 80% of such patients elect repeated angioplasty (with the remaining 20% electing coronary artery bypass graft) and this is added to the cost of coronary artery bypass graft for the remaining 20%, the total cost for restenosis easily reaches into billions of dollars. Thus, successful prevention of restenosis could result not only in significant therapeutic benefit but also in significant health care savings.

Although it is not clear whether elevated MCP-1 expression is the cause or consequence of the above diseases, therapeutic benefit resulted from the application of neutralizing antibodies in a number of animal models.

So far, prior art monoclonal antibodies were screened for their ability to act as receptor antagonists. None of those target the immediate pyroglutamate carrying amino terminus of MCP-1 (=MCP1 N1pE). In this context, it is important to note that deletion of amino acids 1-8 from the N-terminal region completely destroyed MCP-1 activity, suggesting that the amino-terminal region is essential for activity.

It consequently follows, that antibodies directed against the MCP-1 N1pE can play a role not only when investigating the expression and function of MCP-1 but also in therapeutic and diagnostic applications in connection with diseases or disturbances in which MCP-1 might be involved.

In view of the above, one object underlying the present invention is to provide antibodies which are selectively binding to MCP-1 N1pE.

SUMMARY OF THE INVENTION

The present invention provides antibodies selectively binding to MCP-1 N1pE, i.e. pyroglutamate MCP-1.

Preferably, monoclonal antibodies are provided.

The present invention pertains in particular to antibodies or variants thereof, which are characterized in that they bind to the MCP-1 N1pE peptide with a high affinity. Said high affinity means in the context of the present invention an affinity of a $K_D$ value of $10^{-6}$ M or better, preferably a $K_D$ value of $10^{-7}$ M or better, and even more preferably a $K_D$ value of $10^{-8}$ M-$10^{-12}$ M.

Monoclonal antibodies of this type are preferably produced by hybridoma cells. Hybridoma cells of this type were deposited on 06. May 2008 in the Deutsche Sammlung von Mikroorganismen and Zellkulturen (German Collection of Microorganisms and Cell Cultures) GmbH, DSMZ, Inhofenstrasse 7B, 38124 Braunschweig, Germany, in accordance with the Budapest Treaty, namely

| | |
|---|---|
| DSM ACC 2905 | (Hybridoma cell clone 348/1D4) |
| 2906 | (Hybridoma cell clone 348/2C9) |
| 2907 | (Hybridoma cell clone 332/4B8) and |
| 2908 | (Hybridoma cell clone 332/4F8). |

In particular, monoclonal antibodies are preferred, wherein selective binding means a binding to the pyroglutamate carrying amino terminus of MCP-1.

Even preferred are monoclonal antibodies, wherein selective binding means that the antibodies do not show any cross-reactivity with epitopes outside the pyroglutamate carrying amino terminus of MCP-1 N1pE.

The amino terminus of MCP-1 N1pE is defined here as the first 1 to 10 amino acids of the amino terminus of MCP-1 N1pE, preferably the first 1 to 8 amino acids of the amino terminus of MCP N1pE, most preferably the first 1 to 4 amino acids of the amino terminus of MCP N1pE.

The invention relates further to the above hybridoma cell clones per se which possess the ability to produce and release such antibodies.

By means of the antibodies 332-4B8 (DSM ACC 2907), 332-4F8 (DSM ACC 2908), 348-2C9(DSM ACC 2906) and 348-1D4 (DSM ACC 2905), the inventors of the present application have, for the first time, made available monoclonal antibodies, as well as hybridoma cells which produce and release these antibodies, which make it possible to selectively recognize and bind to, and consequently influence MCP-1 N1pE. The antibodies consequently provide the physician and research worker with a versatile means, which is so far unique, for, on the one hand, detecting MCP-1 N1pE, both in cell culture and in the sample obtained from a patient, and, on the other hand, for potential manipulation of MCP-1 N1pE, where appropriate, either using the antibody itself or using specific reagents which are coupled to it.

In this connection, the inventors of the present application have ascertained that the above antibodies 332-4B8, 332-4F8, 348-2C9 and 348-1D4 bind selectively to polypeptides of MCP-1 N1pE starting with amino acids pE-P-D i.e. pyroglutamate-proline-aspartic acid.

The inventors have been able to demonstrate that MCP-1 N1pE is also detected in blood samples (serum, plasma) of mammals, especially of mice, rats and humans, and that MCP-1 N1pE levels are elevated after inflammatory stimuli, which can be reversed by application of selective glutminyl cyclase (QC) inhibitors (e.g. 1-(3-(1H-imidazol-1-yl)propyl)-3-(3,4-dimethoxyphenyl)thiourea-hydrochloride (see particularly the glutaminyl peptide cyclase inhibitors as disclosed in WO 2008/104580).

Consequently, these antibodies are outstandingly suitable for diagnostic and therapeutic purposes, with it being possible to achieve a wide variety of investigations and therapeutic effects.

Accordingly, a further embodiment of the invention relates to a pharmaceutical composition comprising one of the above novel antibodies. Preferably said novel antibody is coupled to a cellular directed therapeutic agent or diagnostic agent.

An antibody according to the invention, which is coupled to a means for detection and thus indirectly to the relevant cells, thereby makes it possible to detect these cells directly, for example using X-ray diagnostic/scintigraphic methods. In a corresponding manner, coupling to a therapeutically active agent can also make it possible to exert a direct and selective effect on MCP-1 N1pE carrying cells.

Further advantages will be evident from the description given below.

It will be understood that the features which are mentioned above, and those which are still to be explained below, can be used not only in the combinations which are in each case specified but also in other combinations, or on their own, without departing from the scope of the present invention.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE PRESENTLY PREFERRED EMBODIMENTS

Definitions

Figure 1A:
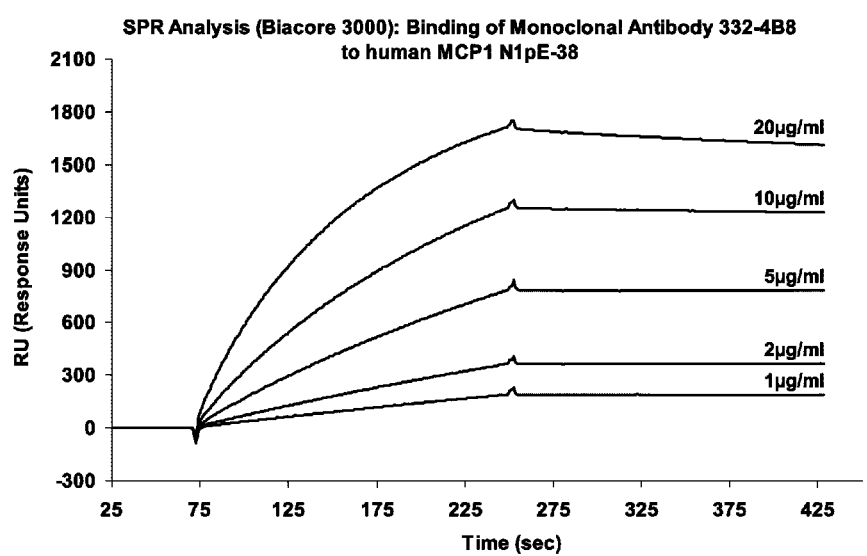
FIG. 1A: Binding characteristics of monoclonal antibody 332-4B8 to human MCP-1 N1pE-38 determined with SPR analysis (Biacore 3000). Measurement was performed by using HBS-EP as running buffer. Association took place for 180 sec, followed by a 180 sec dissociation phase and 5 sec regeneration with 0.1M HCl.

The following definitions and methods are provided to better define the present invention and to guide those of ordinary skill in the art in the practice of the present invention. Unless otherwise noted, terms are to be understood according to conventional usage by those of ordinary skill in the relevant art.

The term "antibody" is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity. The antibody may be an IgM, IgG (e.g. IgG1, IgG2, IgG3 or IgG4), IgD, IgA or IgE, for example. Preferably however, the antibody is not an IgM antibody.

"Antibody fragments" comprise a portion of an intact antibody, generally the antigen binding or variable region of the intact antibody. Examples of antibody fragments include Fab, Fab', F(ab')2, and Fv fragments: diabodies; single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to "polyclonal antibody" preparations, which typically include different antibodies directed against different determinants (epitopes), each monoclonal antibody is directed against a single determinant on the antigen. In addition to their specificity, the monoclonal antibodies can frequently be advantageous in that they are synthesized by the hybridoma culture, uncontaminated by other immunoglobulins. The "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Köhler et al., Nature, 256:495 (1975), or may be made by generally well known recombinant DNA methods. The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein specifically include chimeric antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain a minimal sequence derived from a non-human immunoglobulin. For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences.

These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321:522-525 (1986), Reichmann et al, Nature. 332: 323-329 (1988): and Presta, Curr. Op. Struct. Biel., 2:593-596 (1992). The humanized antibody includes a Primatized™ antibody wherein the antigen-binding region of the antibody is derived from an antibody produced by immunizing macaque monkeys with the antigen of interest.

"Single-chain Fv" or "sFv" antibody fragments comprise the variable heavy chain (VH) and variable light chain (VL) domains of an antibody, wherein these domains are present in a single polypeptide chain. Generally, the Fv polypeptide further comprises a polypeptide linker between the VH and VL domains which enables the sFv to form the desired structure for antigen binding. For a review of sFv see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VD) in the same polypeptide chain (VH-VD). By using a linker that is too short to allow pairing between the two domains on the same chain, the domains are forced to pair with the complementary domains of another chain and create two antigen-binding sites. Diabodies are described more fully in Hollinger et al., Proc. Natl. Acad. Sol. USA, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. The isolated antibody includes the antibody in situ within recombinant cells since at least one component of the antibody's natural environment will not be present. Ordinarily, however, the isolated antibody will be prepared by at least one purification step.

As used herein, the expressions "cell", "cell line," and "cell culture" are used interchangeably and all such designations include progeny. Thus, the words "transformants" and "transformed cells" include the primary subject cell and culture derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, this will be clear from the context.

The terms "polypeptide", "peptide", and "protein", as used herein, are interchangeable and are defined to mean a biomolecule composed of amino acids linked by a peptide bond.

"Homology" between two sequences is determined by sequence identity. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has, for example, 95% identity with a reference sequence of the present invention, the parameters are preferably adjusted so that the percentage of identity is calculated over the entire length of the reference sequence and homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W.R. Pearson (1990), Methods in Enzymology 183, 63-98, appended examples and the program "The WorkBench" (San Diego Supercomputer Center). For this purpose, the "default" parameter settings may be used.

As used herein, a "conservative change" refers to alterations that are substantially conformationally or antigenically neutral, producing minimal changes in the tertiary structure of the mutant polypeptides, or producing minimal changes in the antigenic determinants of the mutant polypeptides, respectively, as compared to the native protein. When referring to the antibodies and antibody fragments of the invention, a conservative change means an amino acid substitution that does not render the antibody incapable of binding to the subject receptor. One of ordinary skill in the art will be able to predict which amino acid substitutions can be made while maintaining a high probability of being conformationally and antigenically neutral. Such guidance is provided, for example in Berzofsky, (1985) Science 229:932-940 and Bowie et al. (1990) Science 247: 1306-1310. Factors to be considered that affect the probability of maintaining conformational and antigenic neutrality include, but are not limited to: (a) substitution of hydrophobic amino acids is less likely to affect antigenicity because hydrophobic residues are more likely to be located in a protein's interior; (b) substitution of physiochemically similar, amino acids is less likely to affect conformation because the substituted amino acid structurally mimics the native amino acid; and (c) alteration of evolutionarily conserved sequences is likely to adversely affect conformation as such conservation suggests that the amino acid sequences may have functional importance. One of ordinary skill in the art will be able to assess alterations in protein conformation using well-known assays, such as, but not limited to microcomplement fixation methods (see, e.g. Wasserman et al. (1961) J. Immunol. 87:290-295; Levine et al. (1967) Meth. Enzymol. 11:928-936) and through binding studies using conformation-dependent monoclonal antibodies (see, e.g. Lewis et al. (1983) Biochem. 22:948-954).

The terms "a" and "an" as used herein are defined to mean "one or more" and include the plural unless the context is inappropriate.

The invention is explained in more detail below with the aid of application examples and implementation examples as well as the Figures.

For diagnostic applications, the antibody typically will be labelled with a detectable moiety. Numerous labels are available which can be generally grouped into the following categories:

(a) Radioisotopes, such as 35S, 14C, 125I, 3H, and 131I. The antibody can be labelled with the radioisotope using the techniques described in Current Protocols in Immunology, Volumes 1 and 2, Gütigen et al., Ed., Wiley-Interscience. New York, N.Y. Pubs., (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in Current Protocols in Immunology, supra for example. Fluorescence can be quantified using a fluorimeter.

(c) Various enzyme-substrate labels are available. Such enzyme generally catalyses a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g, firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase. O-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym (ed Langone & H. Van Vunakis), Academic Press, New York, 73: 147-166 (1981).

Examples of enzyme-substrate combinations include, for example:
(i) Horseradish peroxidase (HRPO) with hydrogen peroxidase as a substrate, wherein the hydrogen peroxidase oxidizes a dye precursor (e.g. orthophenylene diamine (OPD) or 3,3',5,5'-tetramethyl benzidine hydrochloride (TMB));
(ii) alkaline phosphatase (AP) with para-Nitrophenyl phosphate as chromogenic substrate; and
(iii) β-D-galactosidase (β-D-Gal) with a chromogenic substrate (e.g. p-nitrophenyl-β-D-galactosidase) or the fluorogenic substrate 4-methylumbelliferyl-β-D-galactosidase.

Numerous other enzyme-substrate combinations are available to those skilled in the art.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g. digoxin) and one of the different types of labels mentioned above is conjugated with an anti-hapten antibody (e.g. antidigoxin antibody). Thus, indirect conjugation of the label with the antibody can be achieved.

The inventive antibodies need not be labeled, and the presence thereof can be detected using a labeled antibody, which binds to the inventive antibodies.

The antibodies of the present invention may be employed in any known assay method, such as competitive binding assays, direct and indirect sandwich assays, and immunoprecipitation assays (Zola, Monoclonal Antibodies A Manual of Techniques, pp. 147-158 (CRC Press. Inc., 1987).

Competitive binding assays rely on the ability of a labeled standard to compete with the test sample analyte for binding with a limited amount of antibody. The amount of MCP-1 peptide in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. The second antibody may itself be labeled with a detectable moiety (direct sandwich assays) or may be measured using an anti-immunoglobulin antibody that is labeled with a detectable moiety (indirect sandwich assay). For example, one preferable type of sandwich assay is an ELISA assay, in which case the detectable moiety is an enzyme.

For immunohistochemistry analysis, the tissue sample may be fresh or frozen or may be embedded in paraffin and fixed with a preservative such as formalin, for example.

Diagnostic Kits

As a matter of convenience, the antibody of the present invention can be provided in a kit, i.e., a packaged combination of reagents in predetermined amounts with instructions for performing the diagnostic assay. Where the antibody is labelled with an enzyme, the kit will include substrates and cofactors required by the enzyme (e.g. a substrate precursor which provides the detectable chromophore or fluorophore).

In addition, other additives may be included such as stabilizers, buffers (e.g. a blocking buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

The diagnostic kit according to the invention may contain a further biologically active substance as described below. Especially preferred for the use in the diagnostic kit are inhibitors of glutaminyl cyclase.

The diagnostic kit of the invention is especially useful for the detection and diagnosis of MCP-1-related diseases and conditions selected from the group consisting of inflammatory diseases selected from
  a. neurodegenerative diseases, e.g. mild cognitive impairment (MCI), Alzheimer's disease, neurodegeneration in Down Syndrome, Familial British Dementia, Familial Danish Dementia, multiple sclerosis,
  b. chronic and acute inflammations, e.g. rheumatoid arthritis, atherosclerosis, restenosis, pancreatitis,
  c. fibrosis, e.g. lung fibrosis, liver fibrosis, renal fibrosis,
  d. cancer, e.g. cancer/hemangioendothelioma proliferation, gastric carcinomas,
  e. metabolic diseases, e.g. hypertension,
  f. and other inflammatory diseases, e.g. neuropathic pain, graft rejection/graft failure/graft vasculopathy, HIV infections/AIDS, gestosis, tuberous sclerosis.

Preferably, the antibody according to the present invention is especially useful in a diagnostic method to detect MCP-1-related disease, e.g. atheroschlerosis, rheumatoid arthritis, asthma, delayed hypersensitivity reactions, pancreatitis, Alzheimer's disease, lung fibrosis, renal fibrosis, gestosis, graft rejection, neuropathic pain, AIDS and tumors.

Most preferably, the diagnostic kit of the invention is useful for the detection and diagnosis of Alzheimer's disease, or also most preferably a disease selected from atherosclerosis, rheumatoid arthritis, restenosis and pancreatitis, in particular Alzheimer's disease or rheumatoid arthritis.

Preferred according to the present invention is a monoclonal antibody.

More preferably according to the present invention is a monoclonal antibody, wherein the variable part of the light chain of said antibody has a nucleotide sequence selected from SEQ ID NOs: 33, 37 and 41, or an amino acid sequence selected from SEQ ID NOs: 34, 38 and 42.

Alternatively preferred according to the present invention is a monoclonal antibody, wherein the variable part of the heavy chain of said antibody has a nucleotide sequence selected from SEQ ID NOs: 35, 39 and 43, or an amino acid sequence selected from SEQ ID NOs: 36, 40 and 44.

Further preferred according to the present invention is the monoclonal antibody, wherein the variable part of the light chain of said antibody has the nucleotide sequence of SEQ ID NO: 33 or the amino acid sequence of SEQ ID NO: 34, and wherein the variable part of the heavy chain of said antibody has the nucleotide sequence of SEQ ID NO: 35, or the amino acid sequence of SEQ ID NO: 36.

Also preferred according to the present invention is the monoclonal antibody, wherein the variable part of the light chain of said antibody has the nucleotide sequence of SEQ ID NO: 37 or the amino acid sequence of SEQ ID NO: 38, and wherein the variable part of the heavy chain of said antibody has the nucleotide sequence of SEQ ID NO: 39, or the amino acid sequence of SEQ ID NO: 40.

Even preferred according to the present invention is the monoclonal antibody, wherein the variable part of the light chain of said antibody has the nucleotide sequence of SEQ ID NO: 41 or the amino acid sequence of SEQ ID NO: 42, and wherein the variable part of the heavy chain of said antibody has the nucleotide sequence of SEQ ID NO: 43, or the amino acid sequence of SEQ ID NO: 44.

In particular preferred is a monoclonal antibody, which is produced by a hybridoma cell line selected from the following group

| | |
|---|---|
| 348/1D4 | (Deposit No. DSM ACC 2905) |
| 348/2C9 | (Deposit No. DSM ACC 2906) |
| 332/4B8 | (Deposit No. DSM ACC 2907) |
| 332/4F8 | (Deposit No. DSM ACC 2908) |

According to a further preferred embodiment, the antibody can be humanised or is a chimeric antibody or is a human antibody.

Further, the antibody as selected from the above-mentioned group can also be a functional variant of said group.

In the context of the present invention a "functional variant" of the inventive antibody is an antibody which retains the binding capacities, in particular binding capacities with high affinity to a MCP-1 N1pE-38 or functional variant thereof. The provision of such functional variants is known in the art and encompasses the above-mentioned possibilities, which were indicated under the definition of antibodies and fragments thereof.

In a preferred embodiment, the antibody is an antibody fragment, as defined above.

In a further preferred embodiment, the antibody of the invention is an antibody which has the complementarity-determining regions (CDRs) of the above-defined antibodies. Preferably, the antibody can be labeled; possible labels are those as mentioned above and all those known to a person skilled in the art of diagnostic uses of antibodies in particular.

The present invention further relates to a light chain variable region comprising an nucleic acid sequence that is 85%, 86%, 87%, 88%, 89%, 90%, 91%, 92%, 93%, 94%, 95%, 96%, 97%, 98% or 99% identical to a sequence selected from SEQ ID NOs: 33, 37 or 41, or a functional part thereof.

The present invention further relates to a heavy chain variable region comprising an nucleic acid sequence that is 85%, 86%, 87%, 88%, 89%, 90%, 91%, 92%, 93%, 94%, 95%, 96%, 97%, 98% or 99% identical to a sequence selected from SEQ ID NOs: 35, 39 or 43, or a functional part thereof.

Further preferred according to the present invention is a monoclonal antibody including any functionally equivalent antibody or functional parts thereof, which antibody comprises a light chain variable domain comprising an amino acid sequence that is 85%, 86%, 87%, 88%, 89%, 90%, 91%, 92%, 93%, 94%, 95%, 96%, 97%, 98% or 99% identical to a sequence selected from SEQ ID NOs: 34, 38 or 42.

Even preferred according to the present invention is a monoclonal antibody including any functionally equivalent antibody or functional parts thereof, which antibody comprises a heavy chain variable domain comprising an amino acid sequence that is 85%, 86%, 87%, 88%, 89%, 90%, 91%, 92%, 93%, 94%, 95%, 96%, 97%, 98% or 99% identical to a sequence selected from SEQ ID NOs: 36, 40 or 44.

Moreover, the present invention relates to a monoclonal antibody including any functionally equivalent antibody or functional parts thereof, wherein the variable part of the light chain of said antibody comprises an amino acid sequence selected from SEQ ID NOs: 34, 38 and 42 and/or wherein the variable part of the heavy chain of said antibody comprises an amino acid sequence selected from SEQ ID NOs: 36, 40 and 44, wherein the antibody has been altered by introducing at least one, at least two, or at least 3 or more conservative substitutions into at least one of the sequences of SEQ ID NOs: 34, 36, 38, 40, 42 and 44, wherein the antibody essentially maintains its full functionality.

The present invention further relates to an isolated polynucleotide encoding the light chain variable region of the monoclonal antibodies presented herein, wherein said isolated polynucleotide comprises a nucleic acid sequence selected from SEQ ID Nos: 33, 37 and 41.

The present invention also relates to an isolated polynucleotide encoding the heavy chain variable region of the monoclonal antibodies presented herein, wherein said isolated polynucleotide comprises a nucleic acid sequence selected from SEQ ID Nos: 35, 39 and 43.

Moreover, the present invention relates to an isolated peptide of the light chain variable region of the monoclonal antibodies presented herein, wherein said isolated peptide comprises an amino acid sequence selected from SEQ ID Nos: 34, 38 and 42.

Moreover, the present invention relates to an isolated peptide of the heavy chain variable region of the monoclonal antibodies presented herein, wherein said isolated peptide comprises an amino acid sequence selected from SEQ ID Nos: 36, 40 and 44.

In a further preferred embodiment, the present invention relates to an oligonucleotide selected from the group consisting of SEQ ID NOs: 7 to 32.

Preferably, the antibody is immobilised on a solid phase.

The present invention also relates to a composition which comprises the antibody as defined above. In particular, said composition is a composition for a diagnostic use, especially for the diagnosis of MCP-1-related diseases, in particular by detection of MCP-1 N1pE or variants thereof in a biological sample.

In another embodiment, the antibody according to the invention and as described herein before or a fragment thereof, exhibits a binding affinity to MCP-1 N1pE, which is at least 2 times, particularly at least 4 times, particularly at least 10 times, particularly at least 15 times, more particularly at least 20 times, but especially at least 25 times higher than the binding affinity of conventional antibodies.

In still another embodiment, a chimeric antibody or a fragment thereof, or a humanized antibody or a fragment thereof is provided as described herein before, which antibody substantially binds to MCP-1 N1pE in the mammalian, particularly the human brain but, preferably, does not show any significant cross-reactivity with MCP-1 N1pE, in particular with MCP-1 N1pE 3-38.

The present invention relates also to humanized forms of the antibodies as defined above, compositions comprising said humanized antibodies and the use of said compositions for the treatment of MCP-1-related diseases, especially for the treatment of Alzheimer's disease in a mammal, in particular in a human.

The present invention is also directed to the following hybridoma cell lines

| | |
|---|---|
| DSM ACC 2905 | (Hybridoma cell clone 348/1D4) |
| DSM ACC 2906 | (Hybridoma cell clone 348/2C9) |
| DSM ACC 2907 | (Hybridoma cell clone 332/4B8) and |
| DSM ACC 2908 | (Hybridoma cell clone 332/4F8). |

The present invention also pertains to the use of the antibody or the composition comprising the antibody, both as defined above, in an in vitro diagnostic method. In particular, this diagnostic method is directed to diagnosis of MCP-1-related diseases, especially by detecting an MCP-1 N1pE or variants thereof in a biological sample.

Preferably, said sample is a serum sample.

According to another preferred embodiment, said sample is a liquor, cerebrospinal fluid (CSF) or synovial fluid sample.

In a particularly preferred embodiment, the present invention pertains to the following method:

In vitro or in situ diagnostic method for the diagnosis of an MCP-1-related disease or condition, comprising the following steps:
a) contacting an antibody according to the invention with a sample, preferably selected from a serum, liquor or CSF sample, most preferably a serum sample; or a specific body part or body area of a subject suspected to be afflicted with said condition or disease, and
b) detecting binding of the antibody to an MCP-1 N1pE peptide, from the sample.

More particularly, the invention relates to a method of diagnosis of an MCP-1-related disease or condition, comprising detecting the immunospecific binding of an antibody or an active fragment thereof to an MCP-1 N1pE peptide, in a sample or in situ which includes the steps of
(a) bringing the sample or a specific body part or body area suspected to contain the MCP-1 peptide into contact with an antibody, particularly a monoclonal antibody according to the present invention, or a chimeric antibody or a fragment thereof, or a humanized antibody or a fragment thereof according to the invention and as described herein before, and/or a functional part thereof;
(b) allowing the antibody and/or a functional part thereof, to bind to the MCP-1 N1pE peptide to form an immunological complex;
(c) detecting the formation of the immunological complex; and
(d) correlating the presence or absence of the immunological complex with the presence or absence of MCP-1 N1pE peptide in the sample or specific body part or area.

The aforementioned diagnostic methods are especially useful for the detection and diagnosis of MCP-1-related diseases and conditions selected from the group consisting of inflammatory diseases selected from
a. neurodegenerative diseases, e.g. mild cognitive impairment (MCI), Alzheimer's disease, neurodegeneration in Down Syndrome, Familial British Dementia, Familial Danish Dementia, multiple sclerosis,
b. chronic and acute inflammations, e.g. rheumatoid arthritis, atherosclerosis, restenosis, pancreatitis,
c. fibrosis, e.g. lung fibrosis, liver fibrosis, renal fibrosis,
d. cancer, e.g. cancer/hemangioendothelioma proliferation, gastric carcinomas,
e. metabolic diseases, e.g. hypertension,
f. and other inflammatory diseases, e.g. neuropathic pain, graft rejection/graft failure/graft vasculopathy, HIV infections/AIDS, gestosis, tuberous sclerosis.

Preferably, the aforementioned diagnostic methods are useful to detect MCP-1-related disease, e.g. atheroschlerosis, rheumatoid arthritis, asthma, delayed hypersensitivity reactions, pancreatitis, Alzheimer's disease, lung fibrosis, renal fibrosis, gestosis, graft rejection, neuropathic pain, AIDS and tumors.

Most preferably, the aforementioned diagnostic methods are useful for the detection and diagnosis of Alzheimer's disease, or also most preferably a disease selected from atheroerosclerosis, rheumatoid arthritis, restenosis and pancreatitis, in particular Alzheimer's disease or rheumatoid arthritis.

In still another embodiment, the invention relates to a composition comprising the antibody according to the invention, or a chimeric antibody or a fragment thereof, or a humanized antibody or a fragment thereof according to the invention and as described herein before including any functionally equivalent antibody or any derivative or functional parts thereof, in a therapeutically effective amount, in particular a composition which is a pharmaceutical composition optionally further comprising a pharmaceutically acceptable carrier.

In another embodiment of the invention, said composition comprises the antibody in a therapeutically effective amount.

Further comprised by the invention is a mixture comprising an antibody, particularly a monoclonal antibody according to the invention, or a chimeric antibody or a fragment thereof, or a humanized antibody or a fragment thereof according to the invention and as described herein before including any functionally equivalent antibody or any derivative or functional parts thereof, in a therapeutically effective amount and, optionally, a further biologically active substance and/or a pharmaceutically acceptable carrier and/or a diluent and/or an excipient.

In particular, the invention relates to a mixture, wherein the further biologically active substance is a compound used in the medication of a group of diseases and disorders associated with MCP-1, such as an inflammatory diseases selected from
a. neurodegenerative diseases, e.g. mild cognitive impairment (MCI), Alzheimer's disease, neurodegeneration in Down Syndrome, Familial British Dementia, Familial Danish Dementia, multiple sclerosis,
b. chronic and acute inflammations, e.g. rheumatoid arthritis, atherosclerosis, restenosis, pancreatitis,
c. fibrosis, e.g. lung fibrosis, liver fibrosis, renal fibrosis,
d. cancer, e.g. cancer/hemangioendothelioma proliferation, gastric carcinomas,
e. metabolic diseases, e.g. hypertension, and
f. other inflammatory diseases, e.g. neuropathic pain, graft rejection/graft failure/graft vasculopathy, HIV infections/AIDS, gestosis, tuberous sclerosis.

The other biologically active substance or compound may exert its biological effect by the same or a similar mechanism as the antibody according to the invention or by an unrelated mechanism of action or by a multiplicity of related and/or unrelated mechanisms of action.

Generally, the other biologically active compound may include neutron-transmission enhancers, psychotherapeutic drugs, acetylcholine esterase inhibitors, calcium-channel blockers, biogenic amines, benzodiazepine tranquillizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, serotonergic receptor antagonists, CCR2 receptor antagonists and MCP-1 antibodies. With MCP-1 antibodies as other biologically active agent are meant such antibodies, which are binding native MCP-1, i.e. where the N-terminal Glu residue is not cyclized to pGlu.

More particularly, the invention relates to a mixture comprising at least one compound selected from the group consisting of compounds effective against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), α-secretase activators, β- and γ-secretase inhibitors, tau proteins, neurotransmitter, β-sheet breakers, attractants for amyloid beta clearing/depleting cellular components, inhibitors of N-terminal truncated amyloid beta peptides including pyroglutamated amyloid beta 3-42, such as inhibitors of glutaminyl cyclase, anti-inflammatory molecules, or cholinesterase inhibitors (ChEIs) such as tacrine, rivastigmine, donepezil, and/or galantamine, M1 agonists and other drugs including any amyloid or tau modifying drug and nutritive supplements, and nutritive supplements, together with an antibody according to the present invention and, optionally, a pharmaceutically acceptable carrier and/or a diluent and/or an excipient.

The invention further relates to a mixture, wherein the compound is a cholinesterase inhibitor (ChEIs), particularly a mixture, wherein the compound is one selected from the group consisting of tacrine, rivastigmine, donepezil, galantamine, niacin and memantine.

In a further embodiment, the mixtures according to the invention may comprise niacin or memantine together with an antibody according to the present invention and, optionally, a pharmaceutically acceptable carrier and/or a diluent and/or an excipient.

In a further embodiment, the mixtures according to the invention may comprise a glutaminyl cyclase inhibitor together with an antibody according to the present invention and, optionally, a pharmaceutically acceptable carrier and/or a diluent and/or an excipient.

Preferred inhibitors of glutaminyl cyclase are described in WO 2005/075436, in particular examples 1-141 as shown on pp. 31-40. The synthesis of examples 1-141 is shown on pp. 40-48 of WO 2005/075436. The disclosure of WO 2005/075436 regarding examples 1-141, their synthesis and their use as glutaminyl cyclase inhibitors is incorporated herein by reference.

Further preferred inhibitors of glutaminyl cyclase are described in WO 2008/055945, in particular examples 1-473 as shown on pp. 46-155. The synthesis of examples 1-473 is shown on pp. 156-192 of WO 2008/055945. The disclosure of WO 2008/055945 regarding examples 1-473, their synthesis and their use as glutaminyl cyclase inhibitors is incorporated herein by reference.

Further preferred inhibitors of glutaminyl cyclase are described in WO 2008/055947, in particular examples 1-345 as shown on pp. 53-118. The synthesis of examples 1-345 is shown on pp. 119-133 of WO 2008/055947. The disclosure of WO 2008/055947 regarding examples 1-345, their synthesis and their use as glutaminyl cyclase inhibitors is incorporated herein by reference.

Further preferred inhibitors of glutaminyl cyclase are described in WO 2008/055950, in particular examples 1-212 as shown on pp. 57-120. The synthesis of examples 1-212 is shown on pp. 121-128 of WO 2008/055950. The disclosure of WO 2008/055950 regarding examples 1-212, their synthesis and their use as glutaminyl cyclase inhibitors is incorporated herein by reference.

Further preferred inhibitors of glutaminyl cyclase are described in WO2008/065141, in particular examples 1-25 as shown on pp. 56-59. The synthesis of examples 1-25 is shown on pp. 60-67 of WO2008/065141. The disclosure of WO2008/065141 regarding examples 1-25, their synthesis and their use as glutaminyl cyclase inhibitors is incorporated herein by reference.

Further preferred inhibitors of glutaminyl cyclase are described in WO 2008/110523, in particular examples 1-27 as shown on pp. 55-59. The synthesis of examples 1-27 is shown on pp. 59-71 of WO 2008/110523. The disclosure of WO 2008/110523 regarding examples 1-27, their synthesis and their use as glutaminyl cyclase inhibitors is incorporated herein by reference.

Further preferred inhibitors of glutaminyl cyclase are described in WO 2008/128981, in particular examples 1-18 as shown on pp. 62-65. The synthesis of examples 1-18 is shown on pp. 65-74 of WO 2008/128981. The disclosure of WO 2008/128981 regarding examples 1-18, their synthesis and their use as glutaminyl cyclase inhibitors is incorporated herein by reference.

Further preferred inhibitors of glutaminyl cyclase are described in WO 2008/128982, in particular examples 1-44 as shown on pp. 61-67. The synthesis of examples 1-44 is shown on pp. 68-83 of WO 2008/128982. The disclosure of WO 2008/128982 regarding examples 1-44, their synthesis and their use as glutaminyl cyclase inhibitors is incorporated herein by reference.

Further preferred inhibitors of glutaminyl cyclase are described in WO 2008/128983, in particular examples 1-30 as shown on pp. 64-68. The synthesis of examples 1-30 is shown on pp. 68-80 of WO 2008/128983. The disclosure of WO 2008/128983 regarding examples 1-30, their synthesis and their use as glutaminyl cyclase inhibitors is incorporated herein by reference.

Further preferred inhibitors of glutaminyl cyclase are described in WO 2008/128984, in particular examples 1-36 as shown on pp. 63-69. The synthesis of examples 1-36 is shown on pp. 69-81 of WO 2008/128984. The disclosure of WO 2008/128984 regarding examples 1-36, their synthesis and their use as glutaminyl cyclase inhibitors is incorporated herein by reference.

Further preferred inhibitors of glutaminyl cyclase are described in WO 2008/128985, in particular examples 1-71 as shown on pp. 66-76. The synthesis of examples 1-71 is shown on pp. 76-98 of WO 2008/128985. The disclosure of WO 2008/128985 regarding examples 1-71, their synthesis and their use as glutaminyl cyclase inhibitors is incorporated herein by reference.

Further preferred inhibitors of glutaminyl cyclase are described in WO 2008/128986, in particular examples 1-7 as shown on pp. 65-66. The synthesis of examples 1-7 is shown on pp. 66-73 of WO 2008/128986. The disclosure of WO 2008/128986 regarding examples 1-7, their synthesis and their use as glutaminyl cyclase inhibitors is incorporated herein by reference.

In still another embodiment of the invention mixtures are provided that comprise "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with an antibody, particularly a monoclonal antibody according to the invention, but particularly a chimeric antibody or a fragment thereof, or a humanized antibody or a fragment thereof according to the invention and as described herein and, optionally, a pharmaceutically acceptable carrier and/or a diluent and/or an excipient.

In a specific embodiment of the invention, the compositions and mixtures according to the invention and as described herein before comprise the antibody and the biologically active substance, respectively, in a therapeutically effective amount.

Other compounds that can be suitably used in mixtures in combination with the antibody according to the present invention are described in WO 2008/065141 (see especially pages 37/38), including PEP-inhibitors (pp. 43/44), LiCl, inhibitors of dipeptidyl aminopeptidases, preferably inhibitors of DP IV or DP IV-like enzymes (see pp. 48/49); acetylcholinesterase (ACE) inhibitors (see p. 47), PIMT enhancers, inhibitors of beta secretases (see p. 41), inhibitors of gamma secretases (see pp. 41/42), inhibitors of neutral endopeptidase, inhibitors of phosphodiesterase-4 (PDE-4) (see pp. 42/43), TNFalpha inhibitors, muscarinic M1 receptor antagonists (see p. 46), NMDA receptor antagonists (see pp. 47/48), sigma-1 receptor inhibitors, histamine H3 antagonists (se p. 43), immunomodulatory agents, immunosuppressive agents or an agent selected from the group consisting of antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors (e.g. BB 76163), interferon-tau (trophoblastin) and SAIK-MS; beta-amyloid antibodies (see p. 44), cysteine protease inhibitors (see p. 44); MCP-1 antagonists (see pp. 44/45), amyloid protein deposition inhibitors (see p. 42) and beta amyloid synthesis inhibitors (see p. 42), which document is incorporated herein by reference.

In another embodiment, the invention relates to a mixture comprising the antibody, particularly a monoclonal antibody according to the invention, or a chimeric antibody or a fragment thereof, or a humanized antibody or a fragment thereof according to the invention and as described herein before and/or the biologically active substance in a therapeutically effective amount.

The invention further relates to the use of an antibody, particularly a monoclonal antibody according to the invention, but particularly a chimeric antibody or a fragment thereof, or a humanized antibody or a fragment thereof according to the invention and as described herein before and/or a functional part thereof and/or a pharmaceutical composition, or a mixture comprising said antibody, for the preparation of a medicament for treating or alleviating the effects of a group of diseases and disorders associated with MCP-1 such as diseases including, but not limited to, neurological disorders such as Alzheimer's Disease (AD), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration.

More preferably, the present invention relates to the use of an antibody, particularly a monoclonal antibody according to the invention, but particularly a chimeric antibody or a fragment thereof, or a humanized antibody or a fragment thereof according to the invention and as described herein before and/or a functional part thereof and/or a pharmaceutical composition, or a mixture comprising said antibody, for the preparation of a medicament for treating or alleviating the effects of an inflammatory diseases selected from a. neurodegenerative diseases, e.g. mild cognitive impairment (MCI), Alzheimer's disease, neurodegeneration in Down Syndrome, Familial British Dementia, Familial Danish Dementia, multiple sclerosis, b. chronic and acute inflammations, e.g. rheumatoid arthritis, atherosclerosis, restenosis, pancreatitis, c. fibrosis, e.g. lung fibrosis, liver fibrosis, renal fibrosis, d. cancer, e.g. cancer/hemangioendothelioma proliferation, gastric carcinomas, e. metabolic diseases, e.g. hypertension, and f. other inflammatory diseases, e.g. neuropathic pain, graft rejection/graft failure/graft vasculopathy, HIV infections/AIDS, gestosis, tuberous sclerosis.

Also comprised by the present invention is a method for the preparation of an antibody, particularly a monoclonal antibody according to the invention, but particularly a chimeric antibody or a fragment thereof, or a humanized antibody or a fragment thereof according to the invention and as described herein before and/or a functional part thereof and/or a pharmaceutical composition, or a mixture comprising said antibody and/or a functional part thereof, particularly in a therapeutically effective amount, for use in a method of preventing, treating or alleviating the effects of a group of diseases and disorders associated with MCP-1 as defined above comprising formulating an antibody, particularly a monoclonal antibody according to the invention, but particularly a chimeric antibody or a fragment thereof, or a humanized antibody or a fragment thereof according to the invention in a pharmaceutically acceptable form.

Further comprised by the present invention is a method for preventing, treating or alleviating the effects of a group of diseases and disorders associated with MCP-1 as defined above by administering an antibody and/or a functional part thereof, but particularly a humanized antibody and/or a functional part thereof, or a composition or mixture comprising such an antibody and/or a functional part thereof, to an animal or a human affected by such a disorder comprising administering the antibody in a therapeutically effective amount.

Administration and Dosage

The antibody is preferably administered to a mammal in a carrier; preferably a pharmaceutically-acceptable carrier. Suitable carriers and their formulations are described in Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000. Typically, an appropriate amount of a pharmaceutically acceptable salt is used in the formulation to render the formulation isotonic. Examples of the carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibody can be administered to the mammal by injection (e.g., systemic, intravenous, intraperitoneal, subcutaneous, intramuscular, intraportal, intracerebral, intracerebralventricular, and intranasal), or by other methods, such as infusion, which ensure its delivery to the bloodstream in an effective form. The antibody may also be administered by isolated perfusion techniques, such as isolated tissue perfusion, to exert local therapeutic effects. Intravenous injection is preferred.

Effective dosages and schedules for administering the antibody may be determined empirically, and making such determinations is within the skill in the art. Those skilled in the art will understand that the dosage of antibody that must be administered will vary depending on, for example, the mammal that will receive the antibody, the route of administration, the particular type of antibody used and other drugs being administered to the mammal. Guidance in selecting appropriate doses for antibody is found in the literature on therapeutic uses of antibodies, e.g., Handbook of Monoclonal Antibodies, Ferrone et al., eds., Noges Publications, Park Ridge, N.J., 1985, ch. 22 and pp. 303-357; Smith et al. Antibodies in Human Diagnosis and Therapy, Haber et al., eds., Raven Press, New York, 1977, pp. 365-389. A typical daily dosage of the antibody used alone might range from about 1 µg/kg to up to 100 mg/kg of body weight or more per day, depending on the factors mentioned above. Generally, any of the following doses may be used: a dose of at least about 50 mg/kg body weight; at least about 10 mg/kg body weight; at least about 3 mg/kg body weight; at least about 1 mg/kg body weight; at least about 750 µg/kg body weight; at least about 500 µg/kg body weight; at least about 250 ug/kg body weight; at least about 100 µg/kg body weight; at least about 50 µg/kg body weight; at least about 10 µg/kg body weight; at least about 1 µg/kg body weight, or more, is administered. Antibodies may be administered at lower doses or less frequent at the beginning of the treatment to avoid potential side effect.

In some embodiments, more than one antibody may be present. Such compositions may contain at least one, at least two, at least three, at least four, at least five different antibodies (including polypeptides) of the invention.

The antibody may also be administered to the mammal in combination with effective amounts of one or more other therapeutic agents. The antibody may be administered sequentially or concurrently with the one or more other therapeutic agents. The amounts of antibody and therapeutic agent depend, for example, on what type of drugs are used, the pathological condition being treated, and the scheduling and routes of administration but would generally be less than if each were used individually.

Following administration of antibody to the mammal, the mammal's physiological condition can be monitored in various ways well known to the skilled practitioner. The above principles of administration and dosage can be adapted for polypeptides described herein.

A polynucleotide encoding an antibody or a polypeptide described herein may also be used for delivery and expression of the antibody or the polypeptide in a desired cell. It is apparent that an expression vector can be used to direct expression of the antibody. The expression vector can be administered systemically, intraperitoneally, intravenously, intramuscularly, subcutaneously, intrathecally, intraventricularly, orally, enterally, parenterally, intranasally, dermally, or by inhalation. For example, administration of expression vectors includes local or systemic administration, including injection, oral administration, particle gun or catheterized administration, and topical administration. One skilled in the art is familiar with administration of expression vectors to obtain expression of an exogenous protein in vivo. See, e.g., U.S. Pat. Nos. 6,436,908; 6,413,942; and 6,376,471.

Targeted delivery of therapeutic compositions comprising a polynucleotide encoding an antibody of the invention can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol Chem. (1994) 269:542; Zenke et al, Proc. Natl. Acad. Sd. (USA) (1990) 87:3655; Wu et al., J. Biol. Chem. (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides and polypeptides of the present invention can be delivered using gene delivery vehicles. The gene delivery vehicle can be of viral or non-viral origin (see generally, Jolly, Cancer Gene Therapy (1994) 1:51; Kirnura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740; 4,777,127; GB Patent No. 2,200,651; and EP 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0 524 968. Additional approaches are described in Philip, MoI Cell Biol (1994) 14:2411, and in Woffendin, Proc. Natl. Acad. Sci. (1994) 91:1581.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Preparing and Characterizing Monoclonal Antibodies which are Directed Against MCP-1 N1pE The aim was the generation of monoclonal antibodies reactive with the pE-P-D-A (SEQ ID No:3) containing amino acid sequence at the amino terminus of the peptide MCP-1 N1pE-38 (SEQ ID No:4) (which is MCP-1 N1pE with the first 38 amino acids starting from the N-terminus), but not reactive with the peptide MCP-1 D3-38 (SEQ ID No:5) which is the same molecule as MCP-1 N1pE-38 but lacking pE and P at the amino terminus.

For immunisations the peptide pE-P-D-A-I-N-A-P-V-C amide (human MCP-1 N1pE-9 (SEQ ID No:6)) was used. This low molecular weight antigen was conjugated to Bovine Serum Albumin (Purified Fraction V BSA; Pierce) as carrier protein using Sulfo-MBS (Pierce) as cross-linker.

To generate the monoclonal antibodies 8-week-old female BALB/c mice were immunised with the peptide-BSA-conjugate in two different immunisation procedures as shown in table 1:

TABLE 1

Immunisation protocol for generation of monoclonal MCP-1 N1pE antibodies

| Long Time Immunisation (Day) | Short Time Immunisation (Day) | Injection | Doses (µg/mouse) | Adjuvant |
| --- | --- | --- | --- | --- |
| 1 | 1 | Priming (i.p.) | 100 | TiterMax Gold Adjuvant (Sigma Alrich, St. Louis, USA) |
| 30 | 14 | Boost (i.p.) | 100 | TiterMax Gold Adjuvant (Sigma) |
| 60 | 21 | Boost (i.p.) | 50 | Incomplete Freund's Adjuvant (Sigma) |
| 90 | 28 | Boost (i.p.) | 50 | Incomplete Freund's Adjuvant (Sigma) |
| 126 | 35 | Boost (i.v.) | 50 | PBS |
| 129 | 38 | Fusion | | |

For example, 100 µg peptide corresponds to 50 µl of peptide-BSA-conjugate dissolved in PBS. The peptide-BSA-conjugate was emulsified in an equal volume of TiterMax Gold Adjuvant (Sigma) or incomplete Freund's adjuvant and injected as stable emulsion intraperitoneally (i.p.). Three days before the fusion experiment was performed, each mouse received a total dose of 50 µg peptide (25 µl peptide-BSA-conjugate) dissolved in 25 µl PBS given as i.v. injection.

The presence of the desired antibody was detected in the sera of the recipient prior to the final booster dose using the enzyme linked immunosorbent assay (ELISA) with human MCP-1 N1pE-9 as immobilized antigen. The specific antibody titres were greater than 1:200000.

For fusion procedures, $6 \times 10^7$ spleen cells from the immunised mice and $2 \times 10^7$ cells from mouse myeloma cell line SP2/0 were incubated with 1.2 ml of 50% polyethylene glycol (Sigma) for 30 seconds at 37° C. After washing, the cells were seeded in four 96-well cell culture plates. Hybrid clones were selected by growing in HAT medium [RPMI 1640 culture medium (Biochrom, Berlin, DE) supplemented with 20% fetal calf serum (PAN Biotech GmbH, Aigenbach DE) and HAT-Supplement (50×; PAN)].

The culture supernatants were primarily screened for antigen specific IgG antibodies two weeks after fusion. The presence of an antigen specific antibody in the culture supernatants was measured by its binding to the following peptides:
human MCP-1 1-9,
human MCP-1 N1pE-38 or
human MCP-1 D3-38,
especially, attached directly to the wells of a 96-well plate. The antibody binding was quantified by adding the relevant anti-species immunoglobulin (rabbit anti-mouse IgG (HRP) Fc-specific antibody, Pierce, Rockford, USA) to which an enzyme is bound, followed by a chromogenic substrate to that enzyme. Fresh culture medium and a dilution of the polyclonal mouse antiserum were used as negative or as positive controls.

The specific antibody producing hybridoma colonies were transferred into 24-well plates for cell propagation and were tested again. The hybridomas repeated positive for human MCP-1 N1pE-38 and negative for human MCP-1 D3-38 were additionally tested by SPR analysis (Biacore 3000).

The best clones which were selected from those showing high association and low dissociation of bound hMCP1 N1pE-38 and additionally showing no binding to the negative control peptide MCP1 D3-38, were then cloned and recloned by limiting-dilution technique, characterized and frozen. For the isotype characterization the Mouse Monoclonal Antibody Isotyping Kit (Roche) was used.

Two weeks after fusion of splenocytes from a Balb/c mouse immunized with the human MCP-1 N1pE-9-BSA-conjugate (short time immunisation protocol) 44 cell culture supernatants were primarily tested positive for the peptide human MCP-1 N1pE-38 as well as for IgG and negative for the peptide human MCP-1 D3-38. 33 out of 44 hybrids were repeated positive after transferring in 24-well plates and were also tested by SPR analysis (Biacore 3000). 8 hybridomas were cloned by limiting dilution resulting in 18 specific clones from which 8 were recloned. Thereby, two cell lines were established which produced antibodies with strong reactivity to the peptide human MCP-1 N1pE-38 and good binding characteristics as demonstrated by SPR analysis (Biacore 3000). The resulting antibodies were designated 332-4B8 and 332-4F8 and both monoclonals 332-4B8 and 332-4F8 belong to the IgG class with the isotype IgG1.

The fusion of the spleen cells of the long time immunized Balb/c mice with cells from mouse myeloma cell line SP2/0 resulted in 35 cell culture supernatants primarily tested positive for human MCP-1 N1pE-38 as well as for IgG. Out of these 35 primary positive hybridomas 15 were repeated positive after transferring in 24-well plates and were further tested by SPR analysis (Biacore 3000). 4 hybridomas were cloned resulting in 8 specific clones from which 4 were recloned. Finally, two cell lines with a reactivity to the peptide human MCP-1 N1pE-38 but not human MCP-1 D3-38 were established as demonstrated by SPR analysis (Biacore 3000). These two cell lines 348-1D4 and 348-2C9 belong to the IgG class with the isotype IgG2b.

From each of the above clones 10 mg of Protein-G purified antibody was produced and subjected to further characterization experiments. The properties of the various MCP-1 N1pE monoclonal antibodies which were prepared can be taken from the following examples.

Example 2

SPR Analysis (Biacore 3000) of Generated Monoclonal Antibodies Directed Against MCP-1 N1pE Protein-G purified monoclonal antibodies 332-4B8, 332-4F8, 348-1D4 and 348-2C9 were characterized with regard to their binding characteristics to human MCP1 N1pE-38 by SPR analysis. These analyses were performed on a Biacore 3000. To this avail, a CM5 chip was coated with approximately 100 response units (RU) human MCP1 N1pE-38 peptide on flow cell (Fc)2. Fc 4 was coated with 100 RU human MCP1 D3-38 peptide. Fc1 and Fc3 were prepared for blank subtraction. Monoclonal antibodies were diluted in running buffer HBS-EP (Hepes buffered saline+3 mM EDTA+0.0050 (v/v) surfactant P20, Biacore, Freiburg, DE) at concentrations ranging from 20 µg/ml to 1 µg/ml. First, a basal signal was determined with HBS-EP, followed by 180 seconds of application of antibody dilution, to determine association of antibody to antigen. Then pure HBS-EP was injected again for another 180 sec to determine the dissociation rate of the corresponding antibody. Finally, the Biacore CM5 chip was regenerated by a short injection of 0.1M HCl, to remove all residing antibody.

Blank signals from Fc 1 and Fc 3 were subtracted from signals of Fc 2 and Fc 4, respectively.

Results

All tested monoclonal antibodies failed to associate to human MCP-1 D3-38 (data not shown). Regarding association to human MCP-1 N1pE-38, the monoclonal antibodies exhibited different binding characteristics.

The strongest association to human MCP-1 N1pE-38 was demonstrated by 332-4B8. At a concentration of 20 µg/ml nearly 2000 RU could be monitored. Dissociation was almost 0 at a concentration of 5 µg/ml, demonstrating an extremely strong binding of 332-4B8 to its antigen (FIG. 1A).

Figure 1B:
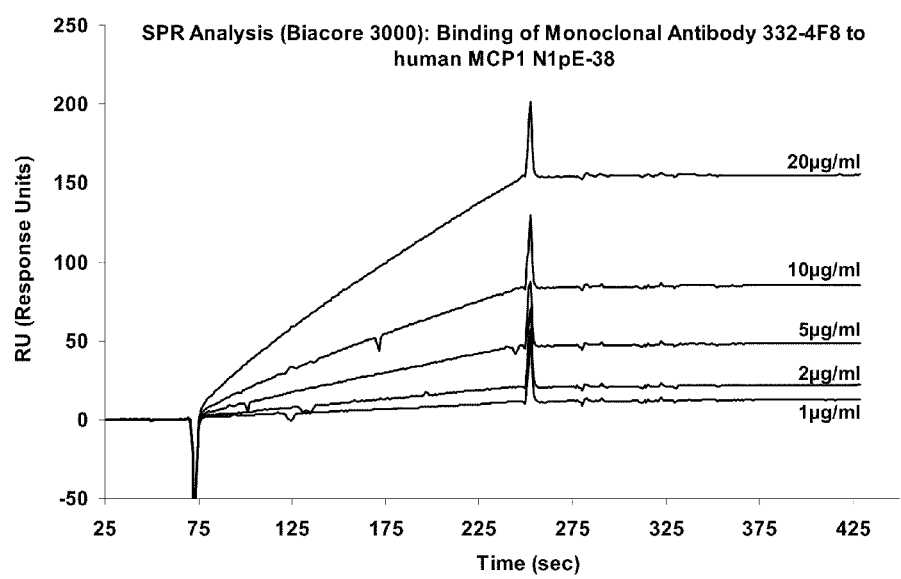
FIG. 1B: Binding characteristics of monoclonal antibody 332-4F8 to human MCP-1 N1pE-38 determined with SPR analysis (Biacore 3000). Measurement was performed by using HBS-EP as running buffer. Association took place for 180 sec, followed by a 180 sec dissociation phase and 5 sec regeneration with 0.1M HCl.

Also, monoclonal antibody 332-4F8 showed a very stable binding to human MCP-1 N1pE-38. However, this antibody clone achieved only about 150 RU within 180 seconds association time. On the other hand, no dissociation occurred at all concentrations tested (FIG. 1B).

Figure 1C:
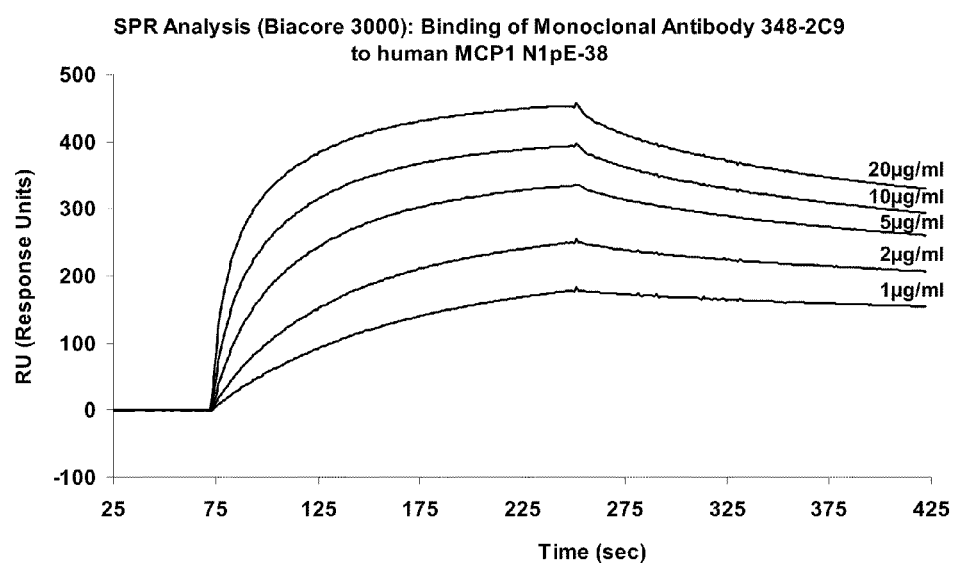
FIG. 1C: Binding characteristics of monoclonal antibody 348-2C9 to human MCP-1 N1pE-38 determined with SPR analysis (Biacore 3000). Measurement was performed by using HBS-EP as running buffer. Association took place for 180 sec, followed by a 180 sec dissociation phase and 5 sec regeneration with 0.1M HCl.
Figure 1D:
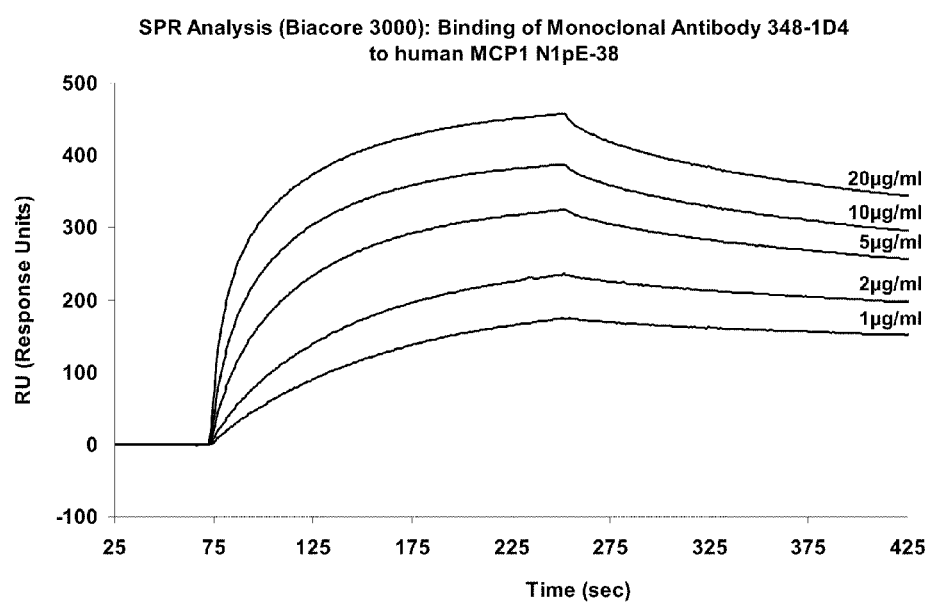
FIG. 1D: Binding characteristics of monoclonal antibody 348-1D4 to human MCP-1 N1pE-38 determined with SPR analysis (Biacore 3000). Measurement was performed by using HBS-EP as running buffer. Association took place for 180 sec, followed by a 180 sec dissociation phase and 5 sec regeneration with 0.1M HCl.
Figure 2A:
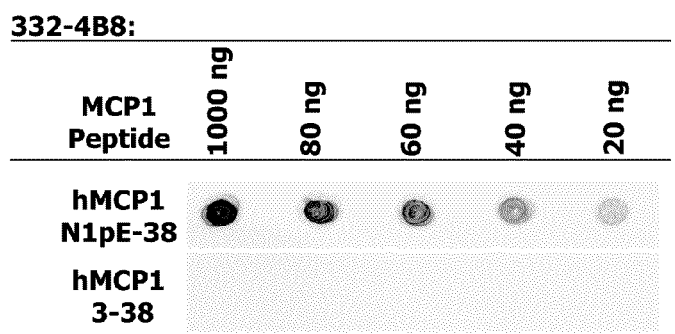
FIG. 2A: DotBlot analysis of monoclonal antibody 332-4B8 to human MCP-1 N1pE-38 and MCP-1 3-38.
Figure 2B:
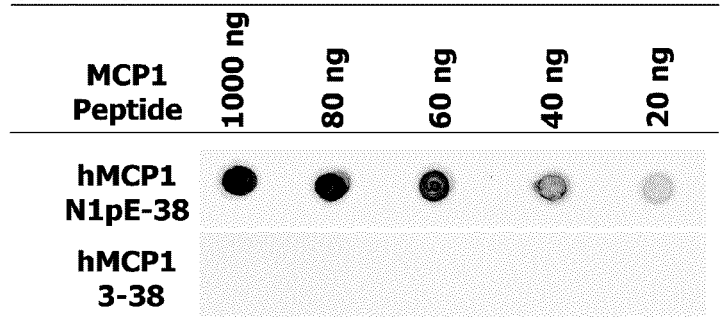
FIG. 2B: DotBlot analysis of monoclonal antibody 332-4F8 to human MCP-1 N1pE-38 and MCP-1 3-38.
Figure 2C:
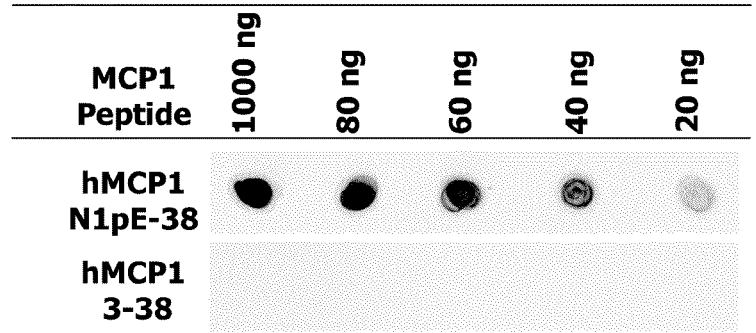
FIG. 2C: DotBlot analysis of monoclonal antibody 348-1D4 to human MCP-1 N1pE-38 and MCP-1 3-38.
Figure 2D:
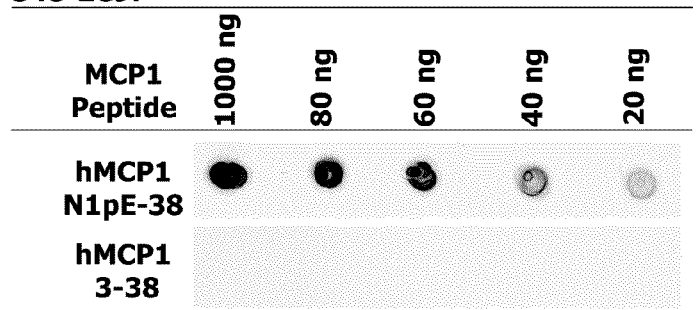
FIG. 2D: DotBlot analysis of monoclonal antibody 348-2C9 to human MCP-1 N1pE-38 and MCP-1 3-38.

Monoclonal antibody clones 348-2C9 and 348-1D4 exhibited almost equal binding characteristics. At 20 µg/ml an association signal of approximately 500 RU was monitored for both clones. Dissociation rate decreased with lower antibody concentrations. Although dissociation was also observable at 1 µg/ml of antibody, the measured signals stayed well above basal line. (FIG. 1C+FIG. 1D).

Taken together the results provide evidence that all monoclonal antibodies tested are able to interact with their corresponding antigen MCP-1 N1pE.

Example 3

Dot Blot Analysis of Generated Monoclonal Antibodies Directed Against MCP-1 N1pE Next it was tested, whether the differences in binding kinetics, as determined by SPR analysis are also evident in an experimental situation where an employed antibody is allowed to interact with its antigen for a prolonged period of time.

A simple DotBlot protocol was accomplished to obtain a general idea about the sensitivity of MCP-1 N1pE antibody clones toward the respective native peptide. Human MCP-1 N1pE-38 and human MCP-1 D3-38 peptides in descending concentrations (1000 ng-20 ng) were spotted onto small pieces of nitrocellulose membranes. For analysis, membranes were blocked for two hours with TBST-M (=TBST (Tris buffered saline+0.05% Tween-20)+50 skimmed milk) at room temperature with gentle shaking. Membranes were incubated over night at 4° C. on a rocking platform with the individual MCP-1 N1pE antibody clones diluted to 1 µg/ml in equal volumes of TBST-M. Secondary anti-mouse antibody conjugated with alkaline phosphatase was used for signal detection, following standard procedures.

Results:

As seen in FIG. 2A-2D, all antibody clones tested revealed almost equal results in the Dot Blot analysis. MCP-1 N1pE-38 peptide concentrations down to 20 ng were clearly detected by protein-G purified monoclonal antibodies 332-4B8, 332-4F8, 348-1D4 and 348-2C9. None of the antibody clones generated cross reactivity with MCP-1 D3-38.

Example 4

PepSpot Analysis of Generated Monoclonal Antibodies Directed Against MCP-1 N1pE

To determine specificity and selectivity of MCP-1 N1pE antibody clones in more detail, PepSpot analysis was performed.

Corresponding PepSpot membranes were prepared by JPT Peptide Technologies GmbH, Berlin (JPT). On these membranes, peptides with the indicated amino acid sequences (see FIG. 3; Z represents pE) were immobilized at a concentration of 1 µg/spot.

For analysis, membranes were blocked for two hours with TBST-M (=TBST+5% skimmed milk) at room temperature with gentle shaking. Membranes were incubated over night at 4° C. on a rocking platform with the individual MCP-1 N1pE antibody clones diluted to 1 µg/ml in equal volumes of TBST-M. Secondary anti-mouse antibody conjugated with alkaline phosphatase was used for signal detection, following standard procedures.

Figure 3:
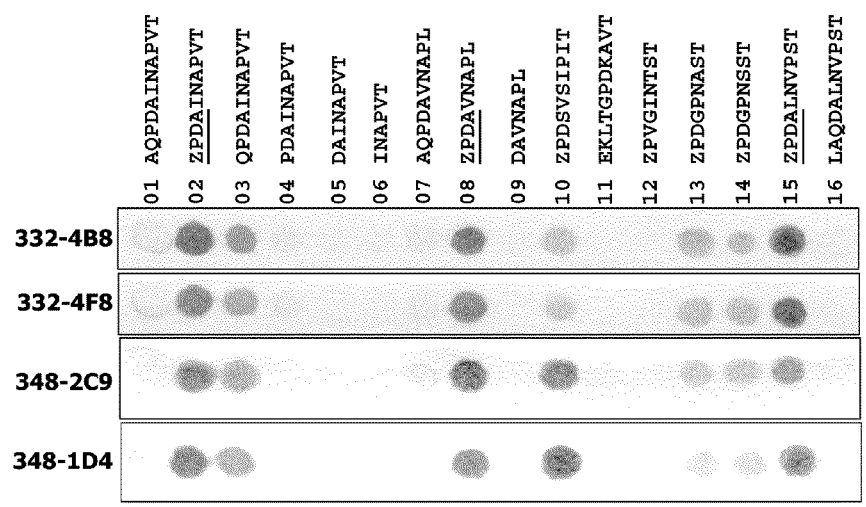
FIG. 3: PepSpot analysis of monoclonal antibodies 332-4B8, 332-4F8, 348-1D4 and 348-2C9.

Results:

As seen in FIG. 3 all four antibody clones tested are highly selective for MCP-1 N1pE peptides. Strong signals were obtained on spots containing MCP-1 N1pE peptides starting with the first 4 amino acids of MCP-1 N1pE (underlined sequences).

In addition, spots with peptides starting with the first three amino acids of MCP-1 N1pE (spots 10, 13 and 14) were clearly recognized by all four antibody clones. Antibodies failed to recognize a peptide starting with only two of the amino terminal amino acids of MCP-1 N1pE (spot 12). Antibodies also failed to recognize peptide spots starting with amino acids different than pE (Z). In case of spot 3, spontaneous formation of pE from Q cannot be excluded. Therefore, signals obtained with this peptide most likely reflect binding of antibody to spontaneously formed pE.

Taken together the results demonstrate that all four MCP-1 N1pE antibody clones require the first 3-4 amino acids of MCP-1 N1pE for binding to the corresponding antigen.

Example 5

Examination of Cross Reactivity to Other Peptides Possessing N1pE Residues by SPR Analysis In order to determine selectivity of the anti MCP-1 N1pE antibodies, cross reactivity to other human Peptides, possessing a N-terminal pE residue was analyzed by surface plasmon resonance.

Therefore, the following peptides or there N-terminal regions were immobilized on the surface of CM5-Chips: MCP-1, MCP-2, big gastrin, gonadoliberin, neurotensin, orexin A, fibronectin, collagen 1 and TRH. As positive control also the binding to MCP-1 N1pE-38 was analyzed. The monoclonal antibodies 332-4B8, 332-4F8, 348-1D4 and 348-2C9 were diluted in HBS-EP (Biacore) down to 25 µg/ml. Cross reactivity was observed using a Biacore 3000 with several CM5-Chips, on which the respective peptides were immobilized. The system was run with 20 µl/min. Measured bulk effects and unspecific reactions to the chip surface were corrected by subtraction of the signal of flow cell 2, 3 or 4, at which the tested peptides were immobilized, with the empty flow cell 1. The association (9 min) was obtained by injection of 180 of the antibody clones. The dissociation was observed over 9 min. Remaining antibody molecules were removed by injection of 5 µl 0.1 M HCL. For every interaction of the antibody with the different peptides the association and dissociation was recorded. Cross reactivity was determined by evaluation of the association phase concerning rate and signal at the end.

Table 2 shows, that the monoclonal antibodies are specific for the MCP-1 N1pE epitope. No cross reactivity with the analysed peptides was observed.

TABLE 2

Investigation of cross reactivity of the monoclonal antibodies 332-4B8, 332-4F8, 348-1D4 and 348-2C9 to several human peptides covering a N-terminal pGlu (pE) residue by SPR analysis.

| pGlu Peptides | % cross reactivity |
| --- | --- |
| MCP-1 (1-38) | 100 |
| MCP-2 | <1 |
| MCP-1 (2-38) | <1 |
| MCP-1 (3-38) | <1 |
| Abeta pE3-40 | <1 |
| Big Gastrin | <1 |
| Gonadoliberin | <1 |
| Neurotensin | <1 |
| Orexin A | <1 |
| Fibronectin | <1 |
| Collagen 1 | <1 |
| TRH | <1 |

Example 6

Determining $K_D$ Values of Monoclonal Antibodies Directed Against MCP-1 N1pE

In order to analyze binding kinetics of the MCP-1 N1pE antibody clones to hMCP-1 N1pE-38, the association constant K, dissociation constant $K_D$, reaction enthalpy $\Delta H$ as well as reaction entropy $\Delta S$ have been determined.

The binding affinities of the anti MCP1 N1pE antibodies 348-1D4 and 332-4B8 to the antigen hMCP-1 N1pE-38 were determined using VP-ITC microcalorimeter (MicroCal). Both antibody clones as well as the hMCP-1 N1pE-38 peptide were dialyzed against 150 mM NaCl, 25 mM $Na_2HPO_4$, 25 mM $KH_2PO_4$, 2 mM EDTA pH 7.4 overnight at 4° C. to ensure the same buffer conditions and avoid background heat by protonation events. Afterwards the concentration of the antibodies and the peptide was calculated from absorbance at 280 nm and the respective extinction coefficient. For the titration experiment with clone 348-1D4, Antibody and hMCP-1 N1pE-38 were used at concentrations of 4.38 µM and 147 µM, respectively. For the titration experiment with clone 332-4B8, Antibody and hMCP-1 N1pE-38 were used at concentrations of 1.86 µM and 64.3 µM, respectively. The binding heat was recorded at 20° C. by titration of 29 injections of 10 µl of antigen into the antibody solution. In order to evaluate the heat development originated by the dilution of the hMCP-1 N1pE-38 peptide, this value was determined by titration into the dialysis buffer using defined conditions and instrument setup. Plotting of data occurred by MicroCal ORIGIN software. The calculated binding heat was corrected by the heat originated by dilution of the antigen. The resulting curve was fitted by the "One Set of Sites" binding model. With this model, the stoichiometry, association constant, reaction enthalpy and reaction entropy can be calculated.

Figure 16:
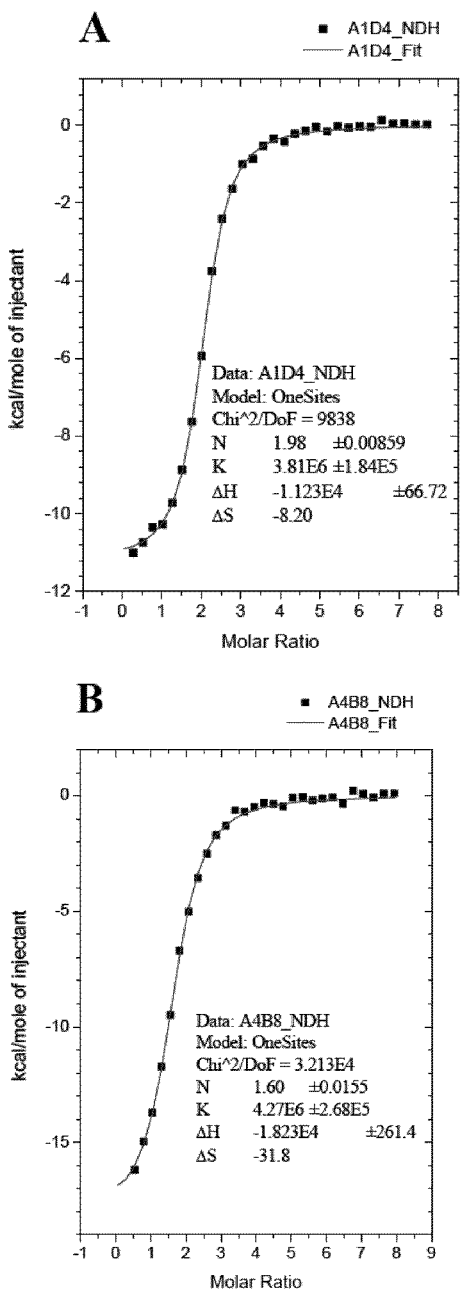
FIG. 16: Fitting curves of the binding heat evolved by titration of the antigen hMCP-1 N1pE-38 to the monoclonal antibodies A—348-1D4 and B—332-4B8.

Results:

FIG. 16 shows the resulting fitting curves and the values calculated for stoichiometry, association constant, reaction enthalpy and reaction entropy. In addition, Table 3 gives an overview about the obtained data.

TABLE 3

Parameter obtained for stoichiometry, association and dissociation constant, reaction enthalpy and reaction entropy after titration of the antigen hMCP-1 N1pE-38 to the monoclonal antibodies 348-1D4 and 332-4B8.

|  | 348-1D4 | 332-4B8 |
|---|---|---|
| Stoichiometry (N) | 1.98 | 1.60 |
| Association Constant (K) in $M^{-1}$ | $3.81 \times 10^6$ | $4.27 \times 10^6$ |
| Dissociation Constant ($K_D$) in M | $2.6 \times 10^{-7}$ | $2.34 \times 10^{-7}$ |
| Reaction Enthalpy ($\Delta H$) in cal/mol | $-1.123 \times 10^4$ | $-1.823 \times 10^4$ |
| Reaction Entropy ($\Delta S$) in cal/mol*K | $-8.20$ | $-31.8$ |

Example 7

Detection of Recombinant Human MCP-1 N1pE in an ELISA by Using Monoclonal Antibodies Directed Against MCP-1 N1pE With the techniques presented so far, selective detection of MCP-1 N1pE could be clearly demonstrated. Therefore the presented antibody clones were also tested for their applicability in tools for potential diagnostic implications, like ELISA.

Consequently, an ELISA protocol was accomplished that allowed detection of recombinant hMCP-1 N1pE.

To capture human MCP-1, commercially available polyclonal antiserum (goat anti-hMCP1-AF (R&D Systems, Minneapolis, USA) as capture antibody which specifically binds human MCP-1 was immobilized in polystyrene 96-well microtitre plates. Unbound capture antibody was washed off the plate. After a blocking step, recombinant hMCP-1 N1pE diluted in blocking buffer was added to the wells. After an incubation period of 2 hours at room temperature, plates were washed at least three times with TBS-T. For detection, MCP-1 N1pE antibody clones (332-4B8, 348-1D4, 348-2C9, respectively) together with HRP-conjugated anti mouse antibody were diluted in blocking buffer, added to the micro titre plate and incubated for 1 hour at room temperature. Following several washes with TBS-T a colour reaction with commercially available HRP substrate TMB (SureBlue Reserve TMB Microwell Peroxidase Substrate (1-component) (KPL, Gaithersburg, USA) was performed (30 minutes incubation at room temperature in the dark) and subsequently stopped by the addition of 1.2N $H_2SO_4$. Absorption was determined by a Tecan Sunrise plate reader.

Figure 4:
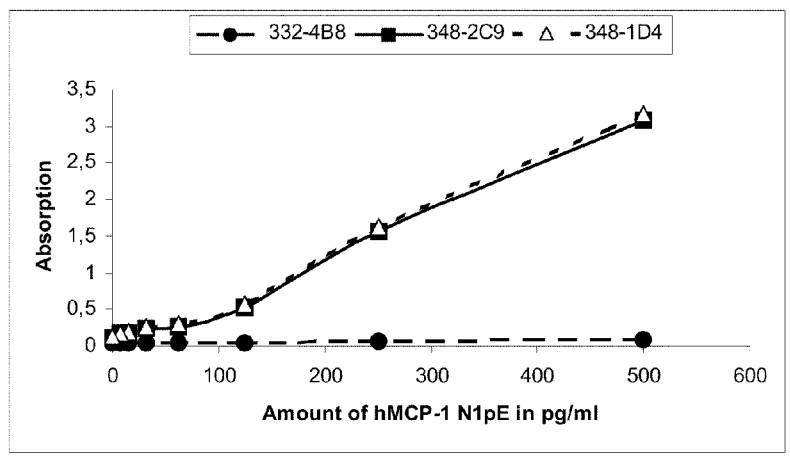
FIG. 4: Quantitative detection of recombinant human MCP-1 N1pE in an ELISA by using the monoclonal anti MCP-1 antibodies 332-4B8, 348-2C9 and 348-1D4.

Results:

The anti MCP-1 antibodies 332-4B8, 348-1D4 and 348-2C9 are able to detect recombinant human MCP-1 in a concentration dependent manner. Thereby, the antibody clones 348-2C9 and 348-1D4 turned out to be much more sensitive in comparison to 332-4B8 (FIG. 4).

Example 8

Detection of MCP-1 N1pE by ELISA in Human Serum Using Monoclonal Antibodies Directed Against MCP-1 N1pE Since recombinant hMCP-1 N1pE can be quantitatively detected in an ELISA by using the monoclonal anti MCP-1 N1pE antibodies of the present invention, the detection of native hMCP-1 N1pE in human serum was tested.

The ELISA protocol corresponds to Example 7, except the usage of FBS, 0.05% Tween, 10% FBS for blocking and dilution steps.

Figure 5:
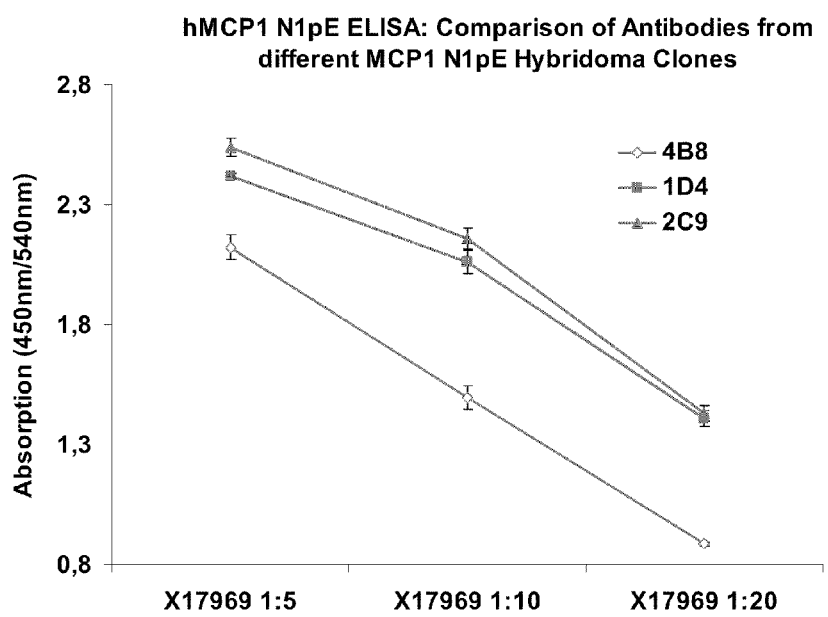
FIG. 5: Detection of human MCP-1 N1 pE from human serum by monoclonal antibodies 332-4B8, 348-1 D4 and 348-2C9 in ELISA.

Results:

All MCP-1 N1pE antibody clones tested, generated very strong signals in the established ELISA set up. Signals decreased with the dilution factor of the serum sample (FIG. 5; Table 4).

The terms "a" and "an" as used herein are defined to mean "one or more" and include the plural unless the context is inappropriate.

TABLE 4

Detection of human MCP-1 N1pE from human serum by monoclonal antibodies 332-4B8, 348-1D4 and 348-2C9 in ELISA.

| Dilution of Human Serum | | | |
|---|---|---|---|
| 1:5 Absorption/SD | 1:10 Absorption/SD | 1:20 Absorption/SD | MCP-1 N1pE Antibody Clone |
| 2.1/0.054 | 1.5/0.048 | 0.9/0.008 | 332-4B8 |
| 2.4/0.012 | 2.1/0.048 | 1.4/0.033 | 348-1D4 |
| 2.5/0.036 | 2.2/0.042 | 1.4/0.034 | 348-2C9 |

Although clone 332-4B8 demonstrated more favourable binding characteristics in SPR analysis (Biacore), clones 348-1D4 and 348-2C9 gave higher signals in the ELISA. According to the obtained data, all antibody clones tested are well suitable for ELISA applications.

Additionally, these data demonstrate that MCP-1 N1pE is detectable also in human serum of healthy individuals.

Example 9

Spike and Recovery of hMCP-1 N1pE in Human Serum

Spike and Recovery experiments were performed in order to validate the quantitative detection of hMCP1 N1pE in human serum.

The ELISA protocol corresponds to Example 8, for detection of hMCP-1 N1pE the antibody 348-2C9 was used. For validation of Spike and Recovery various levels of recombinant hMCP-1 N1pE were spiked in human serum. Recovery was calculated by subtracting the hMCP-1 N1pE value measured in the unspiked serum sample from the spiked samples.

Results:

Table 5 shows Spike and Recovery data in human serum obtained with the 348-2C9 antibody. A Recovery of the spiked hMCP-1 N1pE peptides of 66%-79.4% was found.

TABLE 5

Spike and Recovery of hMCP-1 N1pE in human serum.

| Expected Spike Level of hMCP1 N1pE [ng/ml] | Observed Spike Level of hMCP1 N1pE [ng/ml] | Observed Spike Level of hMCP1 N1pE in % |
|---|---|---|
| 6 | 4.76 | 79.37 |
| 3 | 2.09 | 69.80 |
| 1.5 | 1.05 | 69.81 |
| 0.75 | 0.50 | 66.00 |
| 0.38 | 0.26 | 69.89 |

This table shows the expected spike level in comparison to observed hMCP-1 N1pE concentrations.

These data confirm, that the monoclonal antibody 348-2C9 can be used for the quantitative detection of hMCP1 N1pE in human serum.

Example 10

Detection of Human MCP-1 N1pE in Cell Culture Supernatants of Stimulated NHDF Cells by ELISA Following an inflammatory stimulus, the expression of hMCP-1 is enhanced in Human Normal Dermal Fibroblasts (NHDF). Hence, it can be assumed that also MCP-1 N1pE level are elevated. If this holds true, the amount of MCP-1 N1pE should increase after application of Oncostatin M (OSM) and Interleukin 1β (IL1β) to NHDF.

To prove this, cell culture supernatants of OSM and IL1β stimulated NHDF were subjected to an ELISA analysis as described in Example 7. The antibody 348-1D4 was used for detection of hMCP1 N1pE. NHDF have been stimulated over 14 days and analyzed at different time points in order to examine time dependency of hMCP-1 N1pE secretion.

Figure 6:
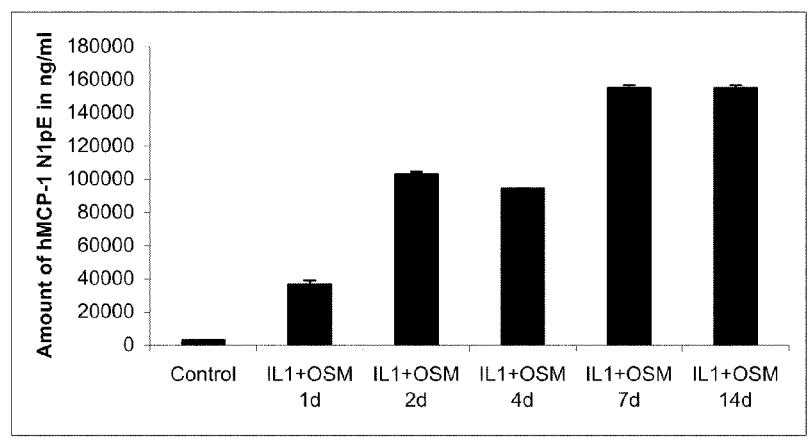
FIG. 6: Time dependent expression of hMCP-1 N1pE in NHDF cells, stimulated by OSM and IL1β.

Results:

Following the inflammatory stimulus of OSM and IL1β application, the amount of hMCP1 N1pE increases in a time dependent manner (FIG. 6). These data show, that hMCP-1 N1pE can also be quantitatively detected in cell culture supernatant of NHDF.

Example 11

Detection of Human MCP-1 N1pE in Cell Culture Supernatant of LPS Stimulated Human Acute Monocytic Leukemia Cell Line (THP1) in the Presence of QC Inhibitor QCI As demonstrated in Examples 8-10, native hMCP-1 N1pE can be quantitatively detected in human serum as well as in cell culture supernatants by ELISA, using the monoclonal anti hMCP-1 N1pE antibodies of the present invention. As glutaminyl cyclase (QC) is a prerequisite for MCP-1 N1pE formation on cellular level, inhibition of QC should consequently result in decreased MCP-1 N1pE level.

To prove this, the Human Acute Monocytic Leukemia Cell Line (THP1) was stimulated 24 h with LPS in absence or presence of increasing concentrations of the QC inhibitor QCI. Cell culture supernatants were subjected to ELISA analysis as described in Example 7. The antibody 348-1D4 was used for detection of hMCP1 N1pE.

Figure 7:
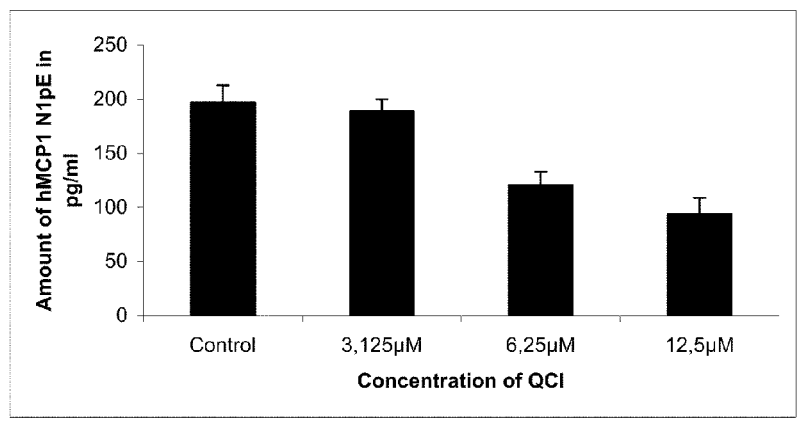
FIG. 7: Concentration dependent reduction of hMCP-1 N1pE in the cell culture supernatant of LPS induced THP1 cells after application of QCI.

Results:

FIG. 7 shows, that the amount of hMCP-1 N1pE decreases with increasing concentrations of QC inhibitor in cell culture supernatant of THP1 cells.

Example 12

Detection of Recombinant Mouse MCP-1 N1pE in an ELISA by Using Monoclonal Antibodies Directed Against MCP-1 N1pE Example 7 shows the concentration dependent detection of recombinant human MCP-1 N1pE by the anti MCP-1 antibodies 332-4B8, 348-1D4 and 348-2C9. Since the four N-terminal amino acids of mouse and human MCP-1 are homologue, the quantitative detection of recombinant mouse MCP-1 was further analysed.

Consequently, an ELISA protocol was accomplished that allowed the detection of recombinant mouse MCP-1 N1pE.

To capture mouse MCP-1, commercially available polyclonal antiserum (rabbit anti mJE (Peprotech, Rocky Hill, USA) as capture antibody which specifically binds mouse MCP-1 was immobilized in polystyrene 96-well microtitre plates. Unbound capture antibody was washed off the plate. After a blocking step, recombinant mMCP-1 N1pE diluted in blocking buffer was added to the wells. After an incubation period of 2 hours at room temperature, plates were washed at least three times with TBS-T. For detection, MCP-1 N1pE antibody clones (332-4B8, 348-1D4, 348-2C9, respectively) together with HRP-conjugated anti mouse antibody were diluted in blocking buffer, added to the micro titre plate and incubated for 1 hour at room temperature. Following several washing steps with TBS-T a colour reaction with commercially available HRP substrate TMB (SureBlue Reserve TMB Microwell Peroxidase Substrate (1-component) (KPL, Gaithersburg, USA) was performed (30 minutes incubation at room temperature in the dark) and subsequently stopped by the addition of 1.2N $H_2SO_4$. Absorption was determined by a Tecan Sunrise plate reader.

Figure 8:
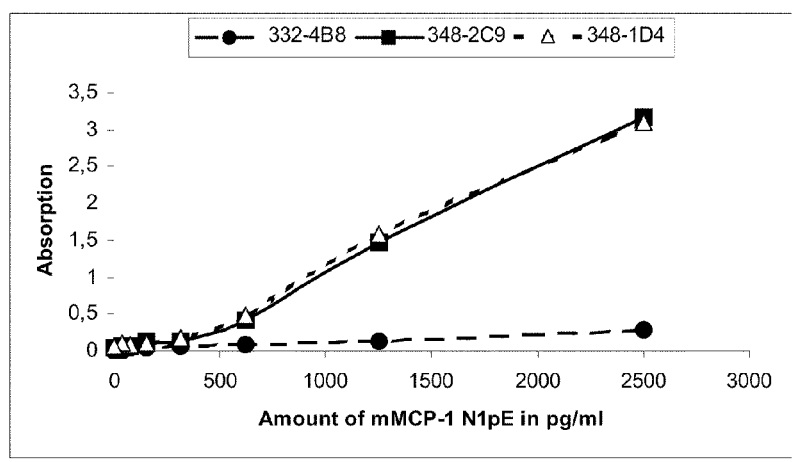
FIG. 8: Quantitative detection of recombinant mouse MCP-1 N1pE in an ELISA by using the monoclonal anti MCP-1 antibodies 332-4B8, 348-2C9 and 348-1D4
Figure 9:
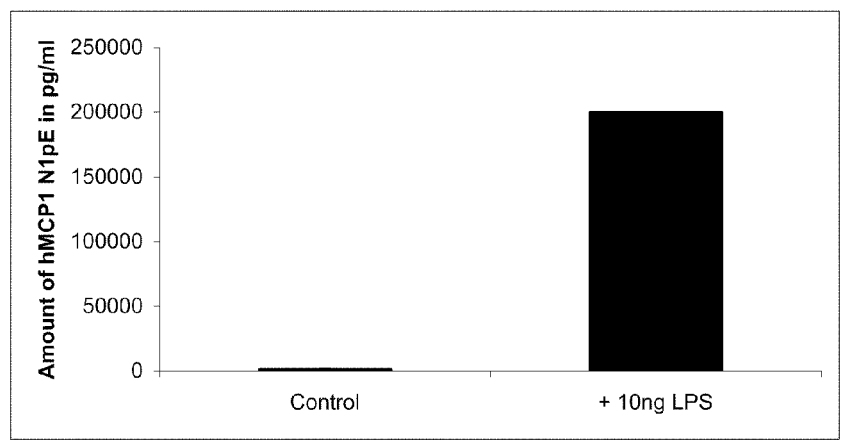
FIG. 9: Quantitative detection of native mouse MCP-1 N1pE in the cell culture supernatant of untreated and LPS induced RAW 264.7 cells.

Results:

The anti MCP-1 antibodies 332-4B8, 348-1D4 and 348-2C9 are able to detect recombinant mouse MCP-1 in a concentration dependent manner. Similar to the results obtained with human hMCP-1, the antibody clones 348-2C9 and 348-1D4 turned out to be much more sensitive in comparison to 332-4B8 (FIG. 8).

Example 13

Detection of Mouse MCP-1 N1pE in Cell Culture Supernatants of a Stimulated Murine Macrophage Cell Line RAW 264.7 by ELISA Following an inflammatory stimulus, the expression of mMCP-1 is enhanced in RAW 264.7 cells. Hence, it can be assumed that also MCP-1 N1pE level are elevated. If this holds true, the amount of mMCP-1 N1pE should increase after application of LPS.

To prove this, cell culture supernatants of LPS stimulated RAW 264.7 were subjected to an ELISA analysis as described in Example 12. The antibody 348-2C9 was used for detection of mMCP1 N1pE. RAW 264.7 cells have been stimulated for 24 h with 10 ng LPS.

Results:

Following the inflammatory stimulus of LPS application, the amount of mMCP1 N1pE increases tremendously (FIG.

9). These data show that mMCP-1 N1pE can also be quantitatively detected in cell culture supernatant of RAW 264.7 cells.

Example 14

Detection of Murine MCP-1 N1pE by ELISA in Cell Culture Supernatants of LPS Stimulated Murine Macrophage Cell Line RAW 264.7 in the Presence of QC Inhibitor QCI Using Monoclonal Antibody 348-2C9

As demonstrated in Example 13, the mMCP-1 N1pE level increases respectably after an inflammatory stimulus like LPS. It could further be shown in Example 11, that the anti MCP-1 N1pE antibodies can be used to demonstrate that the human MCP-1 N1pE level decreases with increasing concentrations of QCI. It has now further been examined if this effect can also be detected in the mouse Macrophage cell line RAW 264.7.

The mouse macrophage cell line RAW 264.7 was stimulated with LPS in the absence or presence of increasing concentrations of the QC inhibitor QCI. Cell culture supernatants were subjected to ELISA analysis as described in Example 12. For detection the antibody 348-2C9 was used.

Figure 10:
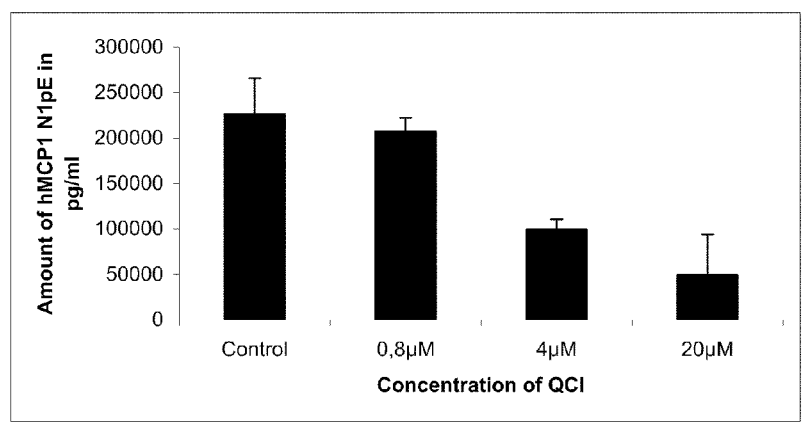
FIG. 10: Concentration dependent reduction of mMCP-1 N1pE in the cell culture supernatant of LPS induced RAW 264.7 cells after application of QCI.

Results:

As postulated before, mMCP-1 N1pE level drops in the presence of the QC inhibitor QCI in LPS stimulated mouse macrophages. The decrease of the signal is strictly dependent on the concentration of QCI (see FIG. 10).

Example 15

Detection of Murine MCP-1 N1pE in Serum of Healthy Mice Versus LPS Treated Mice by ELISA Examples 12-14 show the quantitative detection of recombinant mMCP1 N1pE as well as native mMCP1 N1pE in cell culture supernatant by ELISA. As presented in Examples 8-9, the anti MCP-1 N1pE antibodies can also be used for the detection of MCP-1 N1pE in human serum. Further, the level of MCP-1 N1pE is now determined in mouse serum.

The ELISA protocol corresponds to Example 12, except the usage of FBS, 0.05% Tween, 10% FBS for blocking and dilution steps and the usage of the antibody 348-2C9 for detection.

Figure 11:
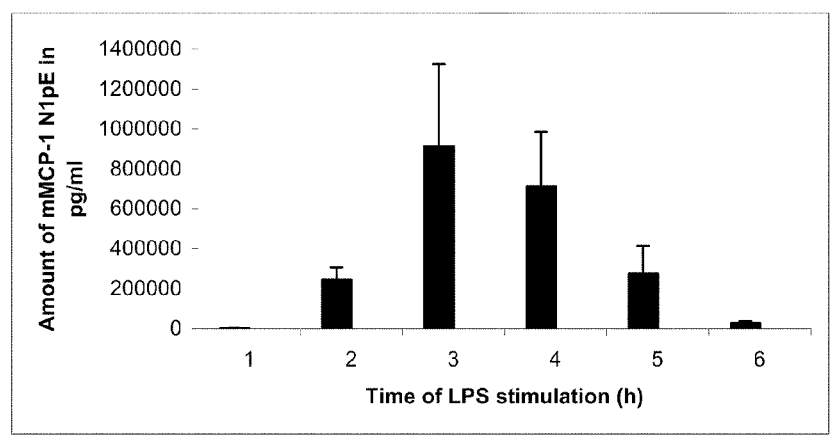
FIG. 11: Quantitative detection of mMCP-1 N1pE in mouse serum after different time points of LPS treatment.

Results:

The mMCP-1 N1pE level in mouse serum increases by LPS stimulation, depending on the time period of stimulation from 400 pg/ml up to 900 ng/ml (FIG. 11). This experiment shows that the antibody 348-2C9 can also be used for the quantitative detection of mMCP-1 N1pE in murine serum.

Example 16

Examination of Dilution Linearity for the Detection of mMCP-1 N1pE in Murine Peritoneal Lavage Fluid by ELISA In order to examine the applicability of the anti MCP-1 N1pE antibodies in the established ELISA, the dilution linearity of Peritoneal Lavage Samples from mice treated with Thioglycollate was analyzed.

The ELISA protocol corresponds to Example 12. For detection, the antibody 348-2C9 was used. To determine assay linearity, each sample was serially diluted with ELISA Blocker to produce values that are within the assay range.

Figure 12:
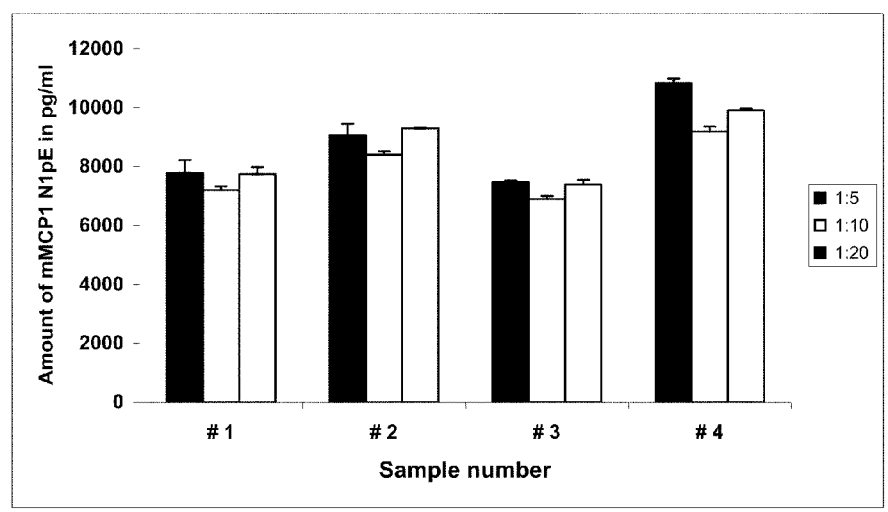
FIG. 12: Dilution Linearity of the quantitative detection of mMCP-1 N1pE in peritoneal lavage fluid from thioglycollate treated mice by ELISA.

Results:

FIG. 12 depicts, that the analysis of different sample dilutions results in similar mMCP-1 N1pE levels with deviations of 15% maximum. This experiment demonstrates, that the anti MCP-1 N1pE antibodies can be used for the analysis of MCP-1 N1pE level in mouse peritoneal lavage fluid.

Example 17

Usage of Anti MCP-1 N1pE Antibodies in Western Blot Analysis and Comparison to Data Obtained by ELISA Examples 3-4 reveal, that the antibodies 332-4F8, 332-4B8, 348-1D4 and 348-2C9 recognize at least the first 4 amino acids of MCP-1 N1pE in Dot Blot and PepSpot analysis. In this experiment, it should be tested whether the antibodies can be used for the detection of native mouse MCP-1 N1pE in cell culture supernatant of RAW 264.7. Furthermore, it should be tested, whether the obtained Western Blot data can confirm the data obtained by ELISA.

For Western Blot analysis, cell culture supernatants of RAW 264.7 cells were subjected to SDS-gelelektrophoresis. Separated proteins were transferred electrically to a nitrocellulose membrane. After blocking of the membrane for two hours with TBST-M at room temperature, antibody incubation occurred over night at 4° C. with the anti MCP-1 N1pE clone 332-4B8 and an antibody recognizing total MCP-1 (goat anti MCP-1, R&D Systems) diluted to 1 µg/ml in TBST-M. Secondary goat anti mouse antibody conjugated with horseradish peroxidase was used for signal detection, following standard procedures.

The ELISA protocol corresponds to Example 14.

Figure 13:
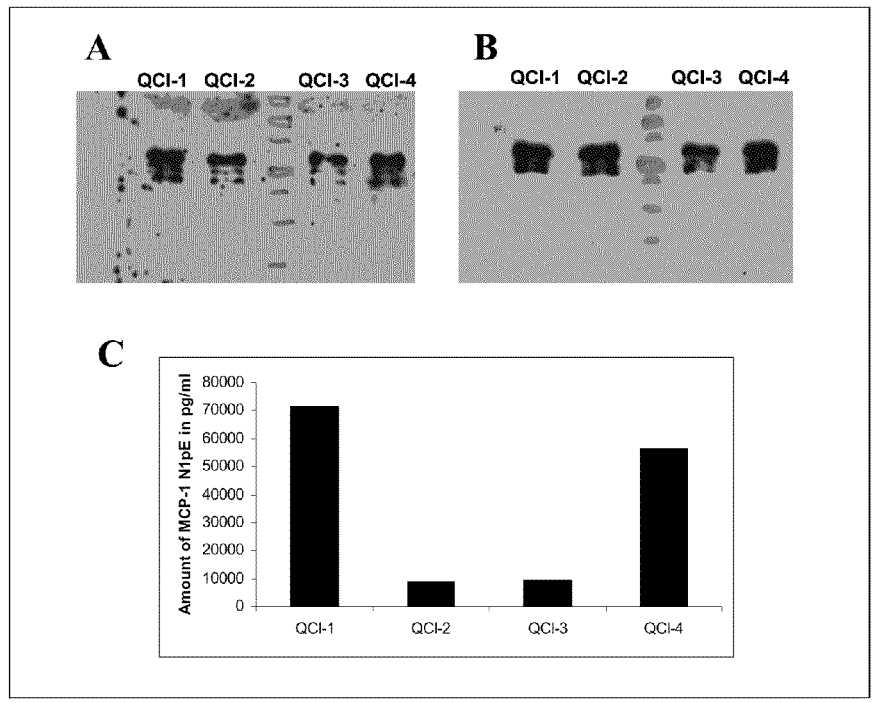
FIG. 13: Comparison of Western Blot signals obtained for murine MCP1 N1pE (A) and total murine MCP1 (B) with the corresponding ELISA Data for murine MCP1 N1pE (C).

Results:

As shown in FIG. 13B, there is no change in the Western Blot signal intensity generated by the antibody goat anti Mouse MCP-1 for the detection of total mMCP-1. However, the Western Blot signal of mMCP-1 N1pE is concentration dependent (FIG. 13A) and correlates with the corresponding ELISA data (FIG. 13C), showing the amount of mMCP-1 N1pE. These data show on the one hand that the anti MCP-1 N1pE antibody 332-4B8 can be used for Western Blot analysis. Furthermore, the correctness of the ELISA data by Western Blot analysis was confirmed.

Example 18

Detection of Recombinant Rat MCP-1 N1pE in an ELISA by Using Monoclonal Antibodies Directed Against MCP-1 N1pE Example 12 shows the concentration dependent detection of recombinant mouse MCP-1 N1pE by the anti MCP-1 antibodies 332-4B8, 348-1D4 and 348-2C9. The N-terminal sequences of mouse and rat MCP-1 are homologue. Therefore, the quantitative detection of recombinant rat MCP-1 was analysed.

Consequently, an ELISA protocol was accomplished that allowed the detection of recombinant rat MCP-1 N1pE.

To capture rat MCP-1, commercially available polyclonal antiserum (rabbit polyclonal to MCP-1 [LS-054182/13136], LifeSpan Biosciences, Seattle, USA) as capture antibody which specifically binds rat MCP-1 was diluted with PBS to 250 ng/ml and immobilized in polystyrene 96-well microtitre plates. Unbound capture antibody was washed off the plate. After a blocking step, recombinant rMCP-1 N1pE diluted in PBS, 0.050 Tween, 10% FBS was added to the wells. After an incubation period of 2 hours at room temperature, plates were washed at least three times with TBS-T. For detection, the MCP-1 N1pE antibody clone 348-2C9 together with HRP-conjugated anti mouse antibody were diluted in PBS, 0.05% Tween, 10% FBS, added to the micro titre plate and incubated for 1 hour at 4° C. Following several washes with TBS-T a colour reaction with commercially available HRP substrate TMB (SureBlue Reserve TMB Microwell Peroxidase Substrate (1-component) (KPL, Gaithersburg, USA) was performed (30 minutes incubation at room temperature in the dark) and subsequently stopped by the addition of 1,2N $H_2SO_4$. Absorption was determined by a Tecan Sunrise plate reader.

Figure 14:
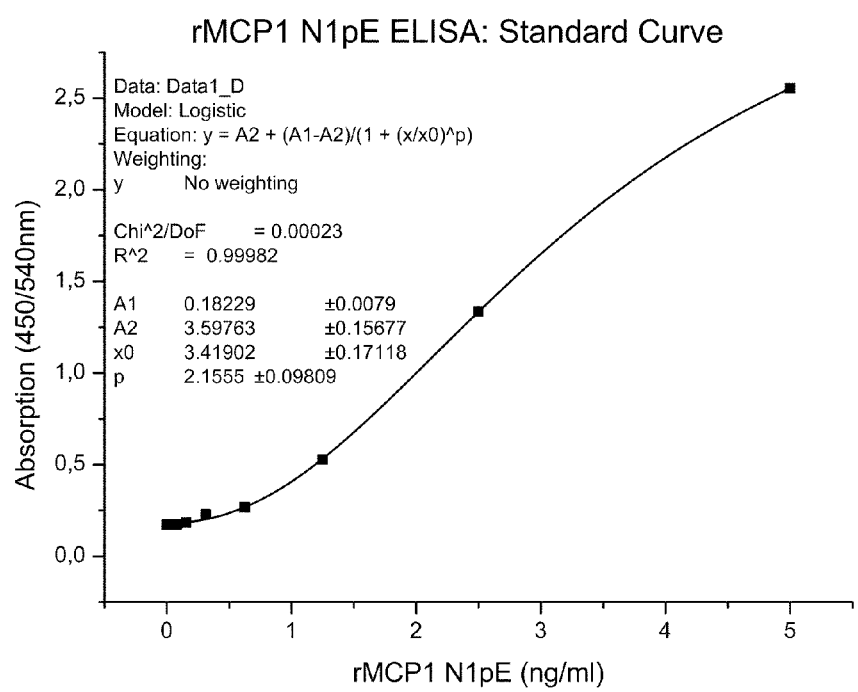
FIG. 14: Quantitative detection of rat MCP-1 N1pE by the anti MCP-1 N1pE antibody 348-2C9 in an ELISA.

Results:

The anti MCP-1 antibody 348-2C9 is able to detect recombinant rat MCP-1 in a concentration dependent manner in an ELISA (FIG. 14).

Example 19

Spike and Recovery of rMCP-1 N1pE in Rat Serum

Example 18 shows the quantitative detection of recombinant rat MCP-1 by the antibody 348-2C9 in an ELISA. In order to proof whether rMCP-1 N1pE can also be detected in rat serum and to validate this ELISA method, Spike and Recovery experiments were performed.

The ELISA protocol corresponds to Example 18, for validation of Spike and Recovery various levels of recombinant rat MCP-1 N1pE were spiked in serum of LPS treated rats. Recovery was calculated by subtracting the rMCP-1 N1pE value measured in the unspiked serum sample from the spiked samples.

Results:

Table 6 shows Spike and Recovery data in rat serum obtained with the 348-2C9 antibody. A Recovery of the spiked rMCP-1 N1pE peptides of 65.50-96.2% was found.

TABLE 6

Spike and Recovery of rMCP-1 N1pE
in serum of LPS stimulated rats.

| Expected Spike Level of rMCP1 N1pE [ng/ml] | Observed Spike Level of rMCP1 N1pE [ng/ml] | Observed Spike Level of rMCP1 N1pE in % |
|---|---|---|
| 2000 | 1485 | 74.23% |
| 1000 | 962 | 96.20% |
| 500 | 327 | 65.49% |
| 250 | 212 | 84.83% |

This table shows the expected spike level in comparison to observed rMCP-1 N1pE concentrations.

These data confirm, that the monoclonal antibody 348-2C9 can be used for the quantitative detection of rat MCP1 N1pE in rat serum.

Example 20

Sequencing Antibody Variable Regions

Cultivation of Hybridoma Cells:

Hybridoma cells were grown in D-MEM (+L-Glutamin, +Na-Pyruvat, 4.5 g/l Glucose, Gibco) with the addition of 15% FBS, 1% MEM-NEA (non essential amino acids, Gibco), 50 µg/ml Gentamycin (Gibco) and 50 µM β-mercaptoethanol at 37° C. and 5% $CO_2$. Subcultivation occurred after 3-4 days depending on cell density. Cells were seeded in a concentration of $0.5 \times 10^6$ cells/ml, splitting occurred at a cell density of $2-5 \times 10^6$ cells/ml.

cDNA Synthesis and Reverse Transcription:

Total RNA was isolated from $2 \times 10^6$ cells according to the manual of the NucleospinRNA Isolation Kit (Macherey-Nagel). 100 ng RNA were applied for cDNA synthesis by using Oligo $(dT)_{15}$ primer (Promega) and SuperScript III Reverse Transcriptase (Invitrogen).

PCR-Amplification of Heavy and Light Chain Variable Regions:

Heavy chain variable regions were amplified from the template cDNA by using Phusion™ High-Fidelity DNA Polymerase (NEW ENGLAND BioLabs) with the primer MHCG1 (in case of clone 5-5-6 and 6-1-6) and MHCG2b (clone 17-4-3 and 24-2-3) in combination with primers MHV1-12. For amplification of light chain variable regions the primer MKC in combination with the primers MKV1-MKV11 were used.

Cloning of PCR Products in pJET1.2:

Heavy and light chain variable regions, amplified by PCR, were cloned into pJET1.2/blunt vector according to the protocol of CloneJET™ PCR Cloning Kit (Fermentas). Sequencing occurred with pJET1.2 sequencing primers. The primer sequences are shown in Table 7.

TABLE 7

Primer sequences

| Primer | Sequence | SEQ ID NO. |
|---|---|---|
| MKV1 | ATGAAGTTGCCTGTTAGGCTGTTGGTGCTG | 7 |
| MKV2 | ATGGAGWCAGACACACTCCTGYTATGGGTG | 8 |
| MKV3 | ATGAGTGTGCTCACTCAGGTCCTGGSGTTG | 9 |
| MKV4 | ATGAGGRCCCCTGCTCAGWTTYTTGGMWTCTTG | 10 |
| MKV5 | ATGGATTTWCAGGTGCAGATTWTCAGCTTC | 11 |
| MKV6 | ATGAGGTKCYYTGYTSAGYTYCTGRGG | 12 |
| MKV7 | ATGGGCWTCAAGATGGAGTCACAKWYYCWGG | 13 |
| MKV8 | ATGTGGGGAYCTKTTTYCMMTTTTTCAATTG | 14 |
| MKV9 | ATGGTRTCCWCASCTCAGTTCCTTG | 15 |
| MKV10 | ATGTATATATGTTTGTTGTCTATTTCT | 16 |
| MKV11 | ATGGAAGCCCCAGCTCAGCTTCTCTTCC | 17 |
| MKC | ACTGGATGGTGGGAAGATGG | 18 |
| MHV1 | ATGAAATGCAGCTGGGGCATSTTCTTC | 19 |
| MHV2 | ATGGGATGGAGCTRTATCATSYTCTT | 20 |
| MHV3 | ATGAAGWTGTGGTTAAACTGGGTTTTT | 21 |
| MHV4 | ATGRACTTTGGGYTCAGCTTGRTTT | 22 |
| MHV5 | ATGGACTCCAGGCTCAATTTAGTTTTCCTT | 23 |
| MHV6 | ATGGCTTGTCYTRGSGCTRCTCTTCTGC | 24 |
| MHV7 | ATGGRATGGAGCKGGRTCTTTMTCTT | 25 |
| MHV8 | ATGAGAGTGCTGATTCTTTTGTG | 26 |
| MHV9 | ATGGMTTGGGTGTGGAMCTTGCTATTCCTG | 27 |
| MHV10 | ATGGGCAGACTTACATTCTCATTCCTG | 28 |

TABLE 7-continued

Primer sequences

| Primer | Sequence | SEQ ID NO. |
|---|---|---|
| MHV11 | ATGGATTTTGGGCTGATTTTTTTTATTG | 29 |
| MHV12 | ATGATGGTGTTAAGTCTTCTGTACCTG | 30 |
| MHCG1 | CAGTGGATAGACAGATGGGGG | 31 |
| MHCG2b | CAGTGGATAGACTGATGGGGG | 32 |

Results:

The following sequences were identified:

Clone 1D4

Light chain variable part, nucleotide sequence
(SEQ ID NO: 33)
ATGGAGTCACAGTTTCTGTTTCTGTTAGTGCTCTGGATTCGGGAAACCAA
CGGTGATGTTGTGATGACCCAGACTCCCCTCAGTTTGTCGGTTACCATTG
GACAACCAGCCTCCATCTCTTGCAAGTCAAGTCAGAGCCTCTTAGATAGT
GCTGGAAAGACATATTTGAGTTGGTTGTTACAGAGGCCAGGCCAGTCTCC
AAAGCGCCTAATCTATCTGGTGTCTAAACTGGACTCTGGAGTCCCTGACA
GGTTCACTGGCAGTGGATCAGGGACAGATTTCACACTGAAAATCAGCAGA
GTGGAGGCTGAGGATTTGGGAGTTTATTACTGCTGGCAAGGTACACATTT
TCCGTGGACGTTCGGTGGAGGCACCAAGCTGGAAATCAAACGGGCTGATG
CTGCACCAACTGTATCCATCTTCCCACCATCCAGT Light chain variable part, protein sequence
(SEQ ID NO: 34)
MESQFLFLLVLWIRETNGDVVMTQTPLSLSVTIGQPASISCKSSQSLLDS
AGKTYLSWLLQRPGQSPKRLIYLVSKLDSGVPDRFTGSGSGTDFTLKISR
VEAEDLGVYYCWQGTHFPWTFGGGTKLEIKRADAAPTVSIFPPSS Heavy chain variable part, nucleotide sequence
(SEQ ID NO: 35)
ATGGAATGGAGCGGGGTCTTTCTCTTCCTCTTGTCAGGAACTGCAGGTGT
CCACTCTGAGGTCCAGCTGCAACAGTCTGGACCTGAGCTGGTGAAGCCTG
GGGCTTCAGTGAAGATGTCCTGTAAGGCTTCTGGATACACATTCACTGAC
TACTACATGGACTGGGTGAAGCAGAGCCATGGAGAAAGCTTTGAGTGCAT
TGGACGTGTTAATCCTTACAATGGTGGTACTAGCTACAACCAGAAGTTCA
AGGGCAAGGCCACATTGACTGTTGACAAGTCCTCCAGCACAGCCTACATG
GAGCTCAACAGCCTGACATCTGAGGACTCTGCGGTCTATTACTGTGCAAG
GCTCGGTAGTAGCTACCGCTGGGGCCAAGGCACCACTCTCACAGTCTCCT
CAGCCAAAACAACACCCCCATCAGTCT Heavy chain variable part, protein sequence
(SEQ ID NO: 36)
MEWSGVFLFLLSGTAGVHSEVQLQQSGPELVKPGASVKMSCKASGYTFTD
YYMDWVKQSHGESFECIGRVNPYNGGTSYNQKFKGKATLTVDKSSTAYM
ELNSLTSEDSAVYYCARLGSSYRWGQGTTLTVSSAKTTPPSV Clone 2C9

Light chain variable part, nucleotide sequence
(SEQ ID NO: 37)
ATGGTGTCCTCAGCTCAGTTCCTGTTTCTGTTAGTGCTCTGGATTCGGGA
AACCAACGGTGATGTTGTGATGACCCAGACTCCCCTCAGTTTGTCGGTTA
CCATTGGACAACCAGCCTCCATCTCTTGCAAGTCAAGTCAGAGCCTCTTA
GATAGTGCTGGAAAGACATATTTGAGTTGGTTGTTACAGAGGCCAGGCCA
GTCTCCAAAGCGCCTAATCTATCTGGTGTCTAAACTGGACTCTGGAGTCC
CTGACAGGTTCACTGGCAGTGGATCAGGGACAGATTTCACACTGAAAATC
AGCAGAGTGGAGGCTGAGGATTTGGGAGTTTATTACTGCTGGCAAGGTAC
ACATTTTCCGTGGACGTTCGGTGGAGGCACCAAGCTGGAAATCAAACGGG
CTGATGCTGCACCAACTGTATCCATCTTCCCACCATCCAGT Light chain variable part, protein sequence
(SEQ ID NO: 38)
MVSSAQFLFLLVLWIRETNGDVVMTQTPLSLSVTIGQPASISCKSSQSLL
DSAGKTYLSWLLQRPGQSPKRLIYLVSKLDSGVPDRFTGSGSGTDFTLKI
SRVEAEDLGVYYCWQGTHFPWTFGGGTKLEIKRADAAPTVSIFPPSS Heavy chain variable part, nucleotide sequence
(SEQ ID NO: 39)
ATGGAATGGAGCGGGATCTTTATCTTCCTCTTGTCAGGAACTGCAGGTGT
CCACTCTGAGGTCCAGCTGCAACAGTCTGGACCTGAGCTGGTGAAGCCTG
GGGCTTCAGTGAAGATGTCCTGTAAGGCTTCTGGATACACATTCACTGAC
TACTACATGGACTGGGTGAAGCAGAGCCATGGAGAAAGCTTTGAGTGCAT
TGGACGTGTTAATCCTTACAATGGTGGTACTAGCTACAACCAGAAGTTCA
AGGGCAAGGCCACATTGACTGTTGACAAGTCCTCCAGCACAGCCTACATG
GAGCTCAACAGCCTGACATCTGAGGACTCTGCGGTCTATTACTGTGCAAG
GCTCGGTAGTAGCTACCGCTGGGGCCAAGGCACCACTCTCACAGTCTCCT
CAGCCAAAACAACACCCCCATCAGTCTATCCACTG Heavy chain variable part, protein sequence
(SEQ ID NO: 40)
MEWSGIFTFLLSGTAGVHSEVQLQQSGPELVKPGASVKMSCKASGYTFTD
YYMDWVKQSHGESFECIGRVNPYNGGTSYNQKFKGKATLTVDKSSSTAYM
ELNSLTSEDSAVYYCARLGSSYRWGQGTTLTVSSAKTTPPSVYPL Clone 4B8

Light chain variable part, nucleotide sequence
(SEQ ID NO: 41)
ATGAAGTTGCCTGTTAGGCTGTTGGTGCTGATGTTCTGGATTCCTGCTTC
CAGCAGTGATGTTTTGATGACCCAAACTCCACTCTCCCTGCCTGTCAGTC
TTGGAGATCAAGCCTCCATCTCTTGCAAATCTAGTCAGAGCATTGTACAT
AGTAATGGAAACACCTATTTAGAATGGTACCTGCAGAAACCAGGCCAGTC
TCCAAAGCTCCTGATCTACAAAGTTTTCAACCGATTTTCTGGGGTCCCAG
ACAGGTTCAGTGGCAGTGGATCAGGGACAGATTTCACACTCAAGATCAGC
AGAGTGGAGGCTGAGGATCTGGGAGTTTATTACTGCTTTCAAGGTTCACA
TGTTCCGTACACGTTCGGAGGGGGGACCAAGCTGGAAATAAAACGGGCTG
ATGCTGCACCAACTGTATCCATCTTCCCACCATCCAGT Light chain variable part, protein sequence
(SEQ ID NO: 42)
MKLPVRLLVLMFWIPASSSDVLMTQTPLSLPVSLGDQASISCKSSQSIVH
SNGNTYLEWYLQKPGQSPKLLIYKVFNRFSGVPDRFSGSGSGTDFTLKIS
RVEAEDLGVYYCFQGSHVPYTFGGGTKLEIKRADAAPTVSIFPPSS Heavy chain variable part, nucleotide sequence
(SEQ ID NO: 43)
ATGGGATGGAGCGGGGTCTTTATTTTAATCCTGTCAGTAACTACAGGTGT
CCACTCTGAGGTCCAGCTGCAGCAGTCTGGACCTGAGCTGGAGAAGCCTG
GCGCTTCAGTGAAGATATCCTGCAAGGCTTCTGGTTACTCATTCACTGGC
TACAACATGAACTGGGTGAAGCAGAACAATGGAAAGAGCCTTGAGTGGAT
TGGAAATATTACTCCTTACTATGGTAGTACTAGCTACAACCAGAAGTTCA
AGGGCAGGGTCACATTGACTGTGGACAAATCCTCCAGCACAGCCTACATG
CAGCTCAAGAGCCTGACATCTGAGGACTCTGCAGTCTATTTCTGCCTCCT
ATGGTTACGACGGGGGGACTATGCTATGGACTACTGGGGTCAAGGAACCT
CAGTCACCGTCTCCTCAGCCAAAACGACACCCCCATCTGTCTATCCACTG Heavy chain variable part, protein sequence
(SEQ ID NO: 44)
MGWSGVFILILSVTTGVHSEVQLQQSGPELEKPGASVKISCKASGYSFTG
YNMNWVKQNNGKSLEWIGNITPYYGSTSYNQKFKGRVTLTVDKSSSTAYM
QLKSLTSEDSAVYFCLLWLRRGDYAMDYWGQGTSVTVSSAKTTPPSVYPL

Example 21

Application of MCP-1 N1pE Antibody Clones for Immunohistochemistry

Figure 15:
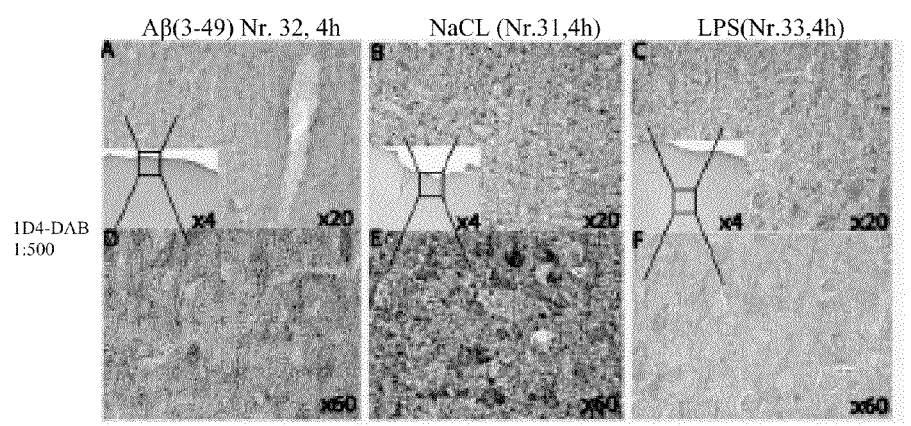
FIG. 15: Staining of MCP-1 N1pE in brain sections of rats with the antibodies 332-4B8, 348-1D4 and 348-2C9 after microinjection of Aβ(3-49), LPS or NaCl.
Figure 15:
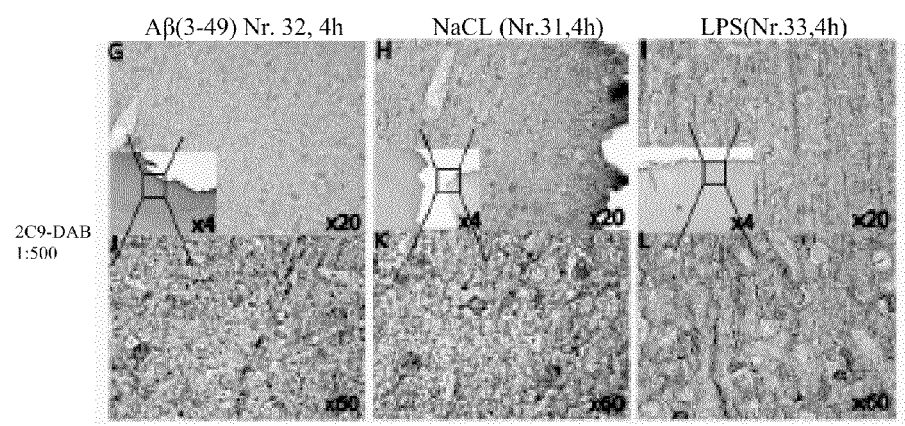
Figure 15:
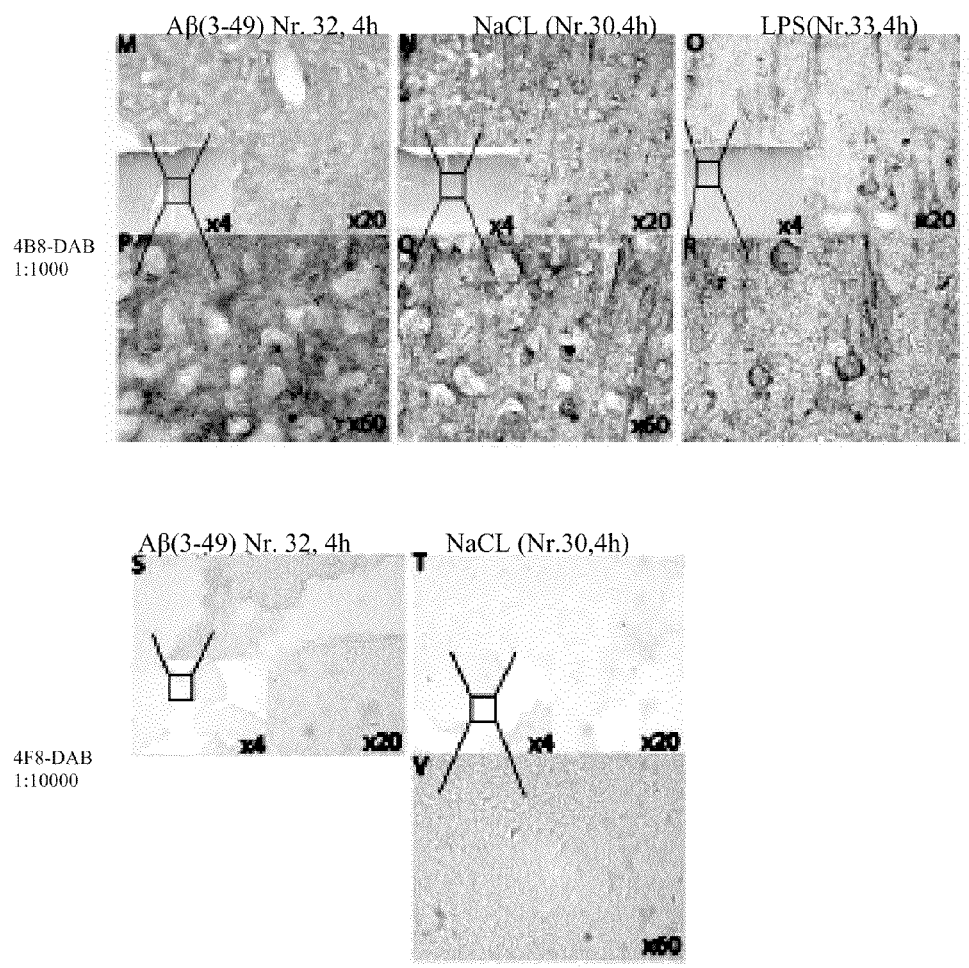

With the antibodies of the present invention, MCP-1 N1pE was stained in brain sections of rats after microinjection of Aβ(3-49), LPS or NaCl. The stained brain sections are shown in FIG. 15. FIG. 15 shows that the antibodies 332-4B8, 348-1D4 and 348-2C9 of the present invention are suitable for immunohistochemistry. The antibodies specifically detect MCP-1 N1pE in brain of rats.

Deposits

Monoclonal antibodies specifically recognizing MCP-1 N1pE, were generated. Currently all corresponding monoclonal antibodies expressing hybridoma cell clones 348/1D4, 348/2C9, 332/4B8 and 332/4F8 have been deposited in accordance with the Budapest Treaty and are available at the Deutsche Sammlung far Mikroorganismen und Zellkulturen (DSMZ) (German Collection of Microorganisms and Cell Cultures) GmbH, Inhoffenstrasse 7B, 38124 Braunschweig, Germany, with a deposit date of May 6, 2008, and with the respective deposit numbers

| | |
|---|---|
| DSM ACC 2905 | (Hybridoma cell clone 348/1D4) |
| DSM ACC 2906 | (Hybridoma cell clone 348/2C9) |
| DSM ACC 2907 | (Hybridoma cell clone 332/4B8) and |
| DSM ACC 2908 | (Hybridoma cell clone 332/4F8). |

Specificity of those antibodies for their respective target sequences could be confirmed. For MCP-1 N1pE, high affinity antibody clones could be identified that should give strong signals in an ELISA set up with an expected detection limit in the low pg range.

What is claimed is:

1. An antibody or an antigen binding fragment thereof, that selectively binds to a pyroglutamate-carrying amino terminus of MCP-1 N1 pE,
wherein the antibody or the antigen binding fragment has substantially no cross-reactivity with an epitope other than the pyroglutamate-carrying amino terminus of MCP-1N1pE.

2. The antibody of claim 1, wherein said antibody is a monoclonal antibody.

3. The antibody of claim 1, wherein said antibody is a chimeric antibody.

4. The antibody to claim 1, wherein a variable part of a light chain of said antibody is encoded by the nucleotide sequence of SEQ ID NO: 33 and has the amino acid sequence of SEQ ID NO: 34, and wherein the variable part of the heavy chain of said antibody is encoded by the nucleotide sequence of SEQ ID NO: 35, and has the amino acid sequence of SEQ ID NO: 36.

5. The antibody according to claim 1,
wherein a variable part of a light chain of said antibody is encoded by a nucleotide sequence of SEQ ID NO: 37 and has the amino acid sequence of SEQ ID NO: 38, and wherein a variable part of a heavy chain of said antibody is encoded by a nucleotide sequence of SEQ ID NO: 39, and has the amino acid sequence of SEQ ID NO: 40.

6. The antibody according to claim 1, wherein a variable part of a light chain of said antibody is encoded by a nucleotide sequence of SEQ ID NO: 41 and has the amino acid sequence of SEQ ID NO: 42, and wherein a variable part of a heavy chain of said antibody is encoded by a nucleotide sequence of SEQ ID NO: 43, and has the amino acid sequence of SEQ ID NO: 44.

7. The antibody according to claim 1, which is produced by hybridoma cells, wherein said hybridoma cells are selected from the group consisting of hybridoma cells deposited with the Deutsche Sammlung für Mikroorganismen and Zellkulturen GmbH, DSMZ as DSM ACC 2905, DSM ACC 2906, DSM ACC 2907 and DSM ACC 2908.

8. The antibody according to claim 1, wherein said antibody is a humanized antibody.

9. The antibody according to claim 1, wherein said antibody is an antibody fragment, which retains a high affinity for MCP-1 N1 pE.

10. The antibody according to claim 1, or an antigen binding fragment thereof, wherein the antibody specificity for MCP-1 N1pE is sufficient for detection of MCP-1 N1 pE or variants thereof in a mammal.

11. The antibody according to claim 10, wherein said mammal is a rat, mouse or a human.

12. The antibody according to claim 1, which is a diabody or a single chain antibody which retains a high affinity to MCP-1 N1 pE.

13. The antibody according to claim 1, wherein complementarity determining regions of the antibodies comprise a complementarity determining region of an antibody produced by hybridoma cells selected from the group consisting of hybridoma cells deposited with the Deutsche Sammlung für Mikroorganismen und Zellkulturen GmbH, DSMZ as DSM ACC 2905, DSM ACC 2906, DSM ACC 2907 and DSM ACC 2908.

14. The antibody according to claim 1, which is labeled.

15. The antibody according to claim 1, which is immobilized on a solid phase.

16. A composition, comprising the antibody or an antigen binding fragment of claim 1.

17. A composition comprising the antibody of claim 1, or an antigen binding fragment thereof and, optionally, at least one of a further biologically active substance, a pharmaceutically acceptable carrier, a diluent, or an excipient.

18. The composition of claim 17, wherein said further biologically active compound is selected from the group consisting of neuron-transmission enhancers, psychotherapeutic drugs, acetylcholine esterase inhibitors, calcium-channel blockers, biogenic amines, benzodiazepine tranquillizers, acetylcholine synthesis, storage or release enhancers, acetylcholine postsynaptic receptor agonists, monoamine oxidase-A or -B inhibitors, N-methyl- D-aspartate glutamate receptor antagonists, non-steroidal anti-inflammatory drugs, antioxidants, serotonergic receptor antagonists, CCR2 receptor antagonists and MCP-1 antibodies.

19. The composition of claim 17, wherein said further biologically active compound is selected from the group consisting of a compound effective against oxidative stress, anti-apoptotic compounds, metal chelators, inhibitors of DNA repair α-secretase activators, tau proteins, neurotransmitter, β-sheet breakers, attractants for amyloid beta clearing/depleting cellular components, inhibitors of N-terminal truncated amyloid beta peptides including pyroglutamated amyloid beta 3-42, inhibitors of glutaminyl cyclase, anti-inflammatory molecules, cholinesterase inhibitors (ChEIs), an amyloid or tau modifying drug, and nutritive supplements.

20. The composition of claim 19, wherein said further biologically active compound is a cholinesterase inhibitor (ChEI).

21. The composition of claim 20, wherein said cholinesterase inhibitor is selected from the group consisting of tacrine, rivastigmine, donepezil, galantamine, niacin and memantine.

22. The composition of claim 19, wherein said further biologically active compound is a glutaminyl cyclase inhibitor.

23. The pharmaceutical composition of claim 22, wherein said glutaminyl cyclase inhibitor is 1-(3-(1H-imidazol-1-yl) propyl)-3-(3,4-dimethoxyphenyl)thiourea-hydrochloride.

24. The composition of claim 17, wherein said further biologically active compound is selected from PEP-inhibitors, LiCl, inhibitors of DP IV or DP IV-like enzymes; acetylcholinesterase (AChE) inhibitors, PIMT enhancers, inhibitors of beta secretases, inhibitors of gamma secretases, inhibitors of neutral endopeptidase, inhibitors of phosphodiesterase-4, TNFalpha inhibitors, muscarinic M1 receptor antagonists, NMDA receptor antagonists, sigma-1 receptor inhibitors, histamine H3 antagonists, immunomodulatory agents, immunosuppressive agents or an agent selected from antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors (e.g. BB 76163), interferon-tau (trophoblastin) and SAIK-MS; beta-amyloid antibodies, cysteine protease inhibitors; MCP-1 antagonists, amyloid protein deposition inhibitors and beta amyloid synthesis inhibitors.

25. A method of producing an antibody that selectively binds to MCP-1 N1pE comprising:
culturing a hybridoma cell selected from the group consisting of hybridoma cells deposited with the Deutsche Sammlung für Mikroorganismen and Zellkulturen GmbH, DSMZ as DSM ACC 2905, DSM ACC 2906, DSM ACC 2907 and DSM ACC 2908; and
isolating an antibody, or an antigen binding fragment thereof, of claim 1.

26. A hybridoma cell line selected from the group consisting of DSM ACC 2905, DSM ACC 2906, DSM ACC 2907 and DSM ACC 2908, all deposited with the Deutsche Sammlung für Mikroorganismen und Zellkulturen GmbH, DSMZ.

* * * * *